US009814679B2

(12) United States Patent
Mohammad

(10) Patent No.: US 9,814,679 B2
(45) Date of Patent: Nov. 14, 2017

(54) TAMPER RESISTANT DOSAGE FORM COMPRISING A MATRIX AND MELT-EXTRUDED PARTICULATES COMPRISING A DRUG

(75) Inventor: Hassan Mohammad, Cambridge (GB)

(73) Assignee: EURO-CELTIQUE S.A., Luxembourg (LU)

( * ) Notice: Subject to any disclaimer, the term of this patent is extended or adjusted under 35 U.S.C. 154(b) by 114 days.

(21) Appl. No.: 13/376,113

(22) PCT Filed: Jun. 7, 2010

(86) PCT No.: PCT/GB2010/050948
§ 371 (c)(1),
(2), (4) Date: Feb. 17, 2012

(87) PCT Pub. No.: WO2010/140007
PCT Pub. Date: Dec. 9, 2010

(65) Prior Publication Data
US 2012/0135075 A1    May 31, 2012

(30) Foreign Application Priority Data
Jun. 5, 2009 (GB) .................................. 0909680.1

(51) Int. Cl.
*A61K 9/20* (2006.01)
*A61K 9/16* (2006.01)
*A61K 31/485* (2006.01)
*A61K 45/06* (2006.01)

(52) U.S. Cl.
CPC .......... *A61K 9/2077* (2013.01); *A61K 9/1617* (2013.01); *A61K 9/1635* (2013.01); *A61K 9/1652* (2013.01); *A61K 9/205* (2013.01); *A61K 9/2031* (2013.01); *A61K 9/2054* (2013.01); *A61K 9/2077* (2013.01); *A61K 31/485* (2013.01); *A61K 45/06* (2013.01)

(58) Field of Classification Search
CPC .. A61K 9/1617; A61K 9/1635; A61K 9/1652; A61K 9/2031; A61K 9/205; A61K 9/2054; A61K 9/2077; A61K 45/06; A61K 31/485; A61K 2300/00
USPC .......................... 424/464, 400, 484; 514/282
See application file for complete search history.

(56) References Cited

U.S. PATENT DOCUMENTS

| 5,958,452 | A | 9/1999 | Oshlack et al. | |
|---|---|---|---|---|
| 6,197,314 | B1 | 3/2001 | Einig | |
| 6,488,961 | B1 | 12/2002 | Robinson et al. | |
| 8,722,086 | B2 | 5/2014 | Arkenau-Marić et al. | |
| 2003/0068375 | A1* | 4/2003 | Wright et al. | 424/468 |
| 2004/0081694 | A1 | 4/2004 | Oshlack et al. | |
| 2004/0228915 | A1 | 11/2004 | Noack et al. | |
| 2005/0031546 | A1 | 2/2005 | Bartholomaus et al. | |
| 2005/0191352 | A1 | 9/2005 | Hayes et al. | |
| 2005/0245483 | A1 | 11/2005 | Brogmann et al. | |
| 2005/0245556 | A1 | 11/2005 | Brogmann et al. | |
| 2006/0193782 | A1 | 8/2006 | Bartholomaus et al. | |
| 2007/0026025 | A1 | 2/2007 | Mitchell | |
| 2007/0026065 | A1 | 2/2007 | Benke et al. | |
| 2007/0259045 | A1 | 11/2007 | Mannion et al. | |
| 2007/0298103 | A1 | 12/2007 | Hayes | |
| 2008/0280921 | A1 | 11/2008 | Dreyer et al. | |
| 2009/0004267 | A1 | 1/2009 | Arkenau-Marić et al. | |
| 2009/0169626 | A1 | 7/2009 | Fleischer et al. | |
| 2010/0151011 | A1 | 6/2010 | Benke | |
| 2011/0288205 | A1* | 11/2011 | Choudhery | 523/439 |
| 2012/0101118 | A1 | 4/2012 | Fleischer et al. | |
| 2012/0108621 | A1 | 5/2012 | Brögmann et al. | |
| 2012/0141583 | A1 | 6/2012 | Mannion et al. | |
| 2012/0183612 | A1 | 7/2012 | Brögmann et al. | |
| 2013/0330409 | A1 | 12/2013 | Mohammad | |

FOREIGN PATENT DOCUMENTS

| CN | 1642529 A | 7/2005 |
|---|---|---|
| CN | 101132772 A | 2/2008 |
| CN | 101374521 A | 2/2009 |
| EP | 0 425 154 A1 | 5/1991 |
| EP | 1 813 276 A1 | 8/2007 |
| GB | 2 418 854 A | 4/2006 |
| GB | 2 447 898 A | 10/2008 |
| NZ | 545202 A | 3/2010 |
| WO | WO 96/14058 A1 | 5/1996 |
| WO | WO 00/76478 A1 | 12/2000 |
| WO | WO 01/58447 A1 | 8/2001 |
| WO | WO 03/013479 A1 | 2/2003 |
| WO | WO 03/032952 A1 | 4/2003 |
| WO | WO 2004/026262 A2 | 4/2004 |
| WO | WO 2005/016314 A1 | 2/2005 |
| WO | WO 2005/079760 A1 | 9/2005 |
| WO | WO 2007/013975 A2 | 2/2007 |
| WO | WO 2007/039122 A2 | 4/2007 |

(Continued)

OTHER PUBLICATIONS

UNC ,1996, "The Pharmaceutics and Compounding Library", "Gels" http://pharmlabs.unc.edu/labs/gels/agents.htm.*
Simpson et al., Current Med. Res. Op. 2008, 24, 3503-3512.*
International Search Report for International Application No. PCT/GB2010/050948, European Patent Office, Netherlands, dated Dec. 1, 2011.
International Preliminary Report on Patentability and Written Opinion for International Application No. PCT/GB2010/050948, The International Bureau of WIPO, Geneva, Switzerland, dated Dec. 15, 2011.
International Search Report and Written Opinion for International Patent Application No. PCT/GB2011/052455, dated Jun. 6, 2012, European Patent Office, Rijswijk, Netherlands.
English language translation of Baoheng, S., et al., "Chapter 42 Gels [Gelling agents]," in *Key Technologies for Modern Preparation Production*, 1st Edition, p. 343, Chemistry Industry Press, China, 2 pages (2006).

(Continued)

*Primary Examiner* — Blessing M Fubara
(74) *Attorney, Agent, or Firm* — Sterne, Kessler, Goldstein & Fox P.L.L.C.

(57) ABSTRACT

The present invention provides a dosage form, particularly a tamper resistant dosage form, comprising: melt-extruded particulates comprising a drug; and a matrix; wherein said melt-extruded particulates are present as a discontinuous phase in said matrix.

41 Claims, 7 Drawing Sheets

(56) References Cited

FOREIGN PATENT DOCUMENTS

| WO | WO 2007/068615 A2 | 6/2007 |
|---|---|---|
| WO | WO 2008/077813 A2 | 7/2008 |
| WO | WO 2010/112203 A1 | 10/2010 |

OTHER PUBLICATIONS

English language translation of Bi, D., "(I) Controlling the drug release by controlling the dissolution rate," "(II) Controlling the drug release by controlling the diffusion process," and "(III) Both diffusion and dissolution control the drug release," in *Pharmaceutics*, 1st Edition, Bi, D., ed., pp. 517-519, China Medical Science and Technology, China, 4 pages (2002).

English language translation of Bi, D., "(I) Treatment of starting materials and excipients," and "(II) Granulation," in *Pharmaceutics*, 4th Edition, Bi, D., ed., p. 326, People's Medical Publishing House, China, 2 pages (2003).

English language translation of Bi, D., "Part 1. Principles and methods of sustained- and controlled release formulations," in *Pharmaceutics*, 5th Edition, Bi, D., ed., paragraphs 3-6 of pp. 395-396 and paragraphs 3-5 of p. 402, People's Medical Publishing House, China, 6 pages (2004).

English language translation of Zhaowang, Z., "III. Grading of powder" and "IV. Device for sifting and separation," in *Traditional Chinese Medicine Pharmaceutics*, 2nd Edition, Zhaowang, Z., ed., p. 64, Traditional Chinese Medicine Publishing House, China, 2 pages (2008).

Restriction Requirement dated Aug. 19, 2015, in U.S. Appl. No. 13/992,946, Mohammad, having a 35 U.S.C. § 371(c) dated Aug. 27, 2013.

Office Action dated Oct. 28, 2015, in U.S. Appl. No. 13/992,946, Mohammad, having a 35 U.S.C. § 371(c) dated Aug. 27, 2013.

Office Action dated Mar. 17, 2016, in U.S. Appl. No. 13/992,946, Mohammad, having a 35 U.S.C. § 371(c) dated Aug. 27, 2013.

Office Action dated Jul. 29, 2016, in U.S. Appl. No. 13/992,946, Mohammad, having a 35 U.S.C. § 371(c) dated Aug. 27, 2013.

Office Action dated Jan. 6, 2017, in U.S. Appl. No. 13/992,946, Mohammad, having a 35 U.S.C. § 371(c) dated Aug. 27, 2013.

\* cited by examiner

TAMPER RESISTANT DOSAGE FORM COMPRISING A MATRIX AND MELT-EXTRUDED PARTICULATES COMPRISING A DRUG

FIELD OF THE INVENTION

The invention relates to dosage forms, in particular tamper-resistant dosage forms, comprising melt-extruded particulates comprising a drug and a matrix, and to methods for making said dosage forms. The invention also concerns the use of the dosage forms in medicine, such as in the treatment of pain.

BACKGROUND TO THE INVENTION

It is generally desirable to provide pharmaceuticals in a tamper-resistant form to maximise the chance that they are taken in the manner intended. This, in turn, ensures that the pharmaceutical is likely to have the full pharmacological effect desired. Even more significantly, the provision of pharmaceuticals in a tamper resistant form means that they are more difficult to abuse.

Pharmaceuticals comprising certain types of drugs are of course more likely to be targeted for abuse than others. For example, dosage forms (e.g. tablets) containing an opioid agonist, a tranquilizer, a CNS depressant, a CNS stimulant or a sedative hypnotic are frequently the targets of abuse, especially dosage forms containing an opioid agonist.

Opioid analgesics are important pharmaceuticals for the treatment and management of pain. Abusers generally aim to modify dosage forms containing opioid analgesics, particularly controlled-release dosage forms, and then administer them in such a way that a high in vivo concentration is achieved over a short period of time so as to experience a euphorogenic effect. Opioid-containing controlled-release tablets may, for example, be crushed in order to make the opioid present therein available for immediate release upon oral or nasal administration. Another form of abuse that occurs is the extraction of opioid from opioid-containing formulations mainly by using ethanol although other solvents, e.g. water or acetone, are also used. The resulting solution may then be crudely administered by injection. Additionally, abusers sometimes disregard the instructions for use of opioid-containing dosage forms and concomitantly imbibe alcohol when taking the dosage form to enhance drug release. This may result in an abuser receiving a dose of opioid more rapidly than intended.

To minimise the possibility that abuse occurs, it has been proposed to formulate opioid analgesics into tablets with high molecular weight polyethylene oxide (PEO). The PEO would serve to control the rate of release of opioid from the dosage form and to impart crush resistance to it. The PEO would also ensure that, if the dosage form is subjected to ethanol extraction, a viscous solution would result that is resistant to syringing and injection.

The amount of PEO, and in particular its ratio to drug and other excipients (if present) in the dosage form, that is necessary to achieve control of release rate and crush resistance is, however, limiting. In particular, it is difficult to prepare high strength dosage forms (i.e. dosage forms containing relatively high amounts of drug) as the amount of PEO required to control the release rate of the drug therefrom and provide crush resistance is impractically high. The dosage form (e.g. tablet) becomes too large and heavy for easy administration. As a result, it is difficult to provide extended-release dosage forms, especially those releasing drug over 24 hours, that are also tamper resistant.

Melt extruded multiparticulates comprising opioid analgesics are also known. These are described, for example, in WO2005/079760. Some of the polymers present in such multiparticulates to facilitate melt extrusion may confer upon the multiparticulates a certain level of crush resistance. Indeed it is known that the higher the level of such polymers present in such multiparticulates the more resilient they are to crushing.

On the other hand, however, the above-described multiparticulates are still somewhat susceptible to abuse by alcohol extraction. It is known, for example, that these multiparticulates release 2 to 3 times more opioid in the presence of alcohol than in its absence. It is thought that this is caused by drug release occurring from the surfaces created by cutting the melt extrudate during the pelletisation process to produce multiparticulates. This is, however, highly undesirable when the likelihood of abuse is relatively high.

Accordingly, there is a need for alternative dosage forms and especially for tamper resistant dosage forms that possess crush resistance as well as resistance to solvent (e.g. ethanol) extraction. The dosage form should advantageously be of a shape, size and weight that can be taken orally with ease. Of course, the dosage form should also be easy to make in a cost effective manner.

It has now been surprisingly found that if melt-extruded particulates comprising a drug are incorporated into a matrix and the mixture is formed into a dosage form (e.g. a tablet), the dosage form possesses excellent alcohol-extraction resistance properties (i.e. tamper resistance) as well as crush resistance. The matrix in which the particulates are present provides resistance to alcohol extraction by forming a gel or viscous solution on exposure to alcohol that resists syringing or injection. The composition and size of the particulates comprising drug provide crush resistance thus even if the matrix is a crushable material, all that can be obtained are the particulates that are difficult to separate and too small to easily crush further but too large for nasal administration. The matrix may also comprise a curable polymer and, in this case, the matrix advantageously provides the overall dosage form with crush resistance.

SUMMARY OF THE INVENTION

Thus viewed from a first aspect the present invention provides a dosage form comprising:
melt-extruded particulates comprising a drug; and
a matrix;
wherein said melt-extruded particulates are present as a discontinuous phase in said matrix.

In preferred dosage forms of the present invention the particulates are stretched particulates. Particularly preferably the particulates are prepared by stretching and cutting a melt extrudate.

Further preferred dosage forms of the invention comprise 15-80% wt of said particulates, based on the total weight of the dosage form. Still further preferred dosage forms comprise 20-85% wt of said matrix, based on the total weight of the dosage form.

In still further preferred dosage forms the matrix comprises a continuous phase comprising a gel-forming agent, particularly a cured gel-forming agent.

Viewed from another aspect the present invention provides a process for preparing a dosage form comprising a drug comprising:

mixing melt-extruded particulates comprising a drug with a matrix material so that said particulates form a discontinuous phase in said matrix and forming said mixture into a dosage form.

Viewed from another aspect the present invention provides a process for preparing a dosage form comprising a drug comprising:
mixing melt-extruded particulates, that are prepared by optionally (e.g. preferably) stretching and cutting a melt extrudate comprising a drug, with a matrix material so that said particulates form a discontinuous phase in said matrix and forming said mixture into a dosage form.

Viewed from another aspect, the present invention provides a process for preparing a dosage form comprising a drug comprising:
  i) melt extruding a composition comprising said drug to form a melt extrudate;
  ii) optionally, e.g. preferably, stretching said melt extrudate to form a stretched extrudate;
  iii) cutting said stretched extrudate to form particulates;
  iv) mixing said particulates with a matrix material so that said particulates form a discontinuous phase in said matrix; and
forming said mixture into a dosage form.

Viewed from a further aspect, the present invention provides a melt extrudate comprising a drug, wherein said extrudate has a diameter of less than about 1 mm.

Preferred extrudates are stretched extrudates.

Viewed from a further aspect, the present invention provides particulates comprising a drug, wherein said particulates have a diameter and/or length of less than about 1 mm.

Preferred particulates are melt-extruded particulates. Particularly preferred particulates are stretched, melt-extruded particulates.

Viewed from a further aspect, the present invention provides particulates comprising a drug, wherein said particulates are obtainable by
  i) melt extruding a composition comprising said drug to form a melt extrudate;
  ii) optionally, e.g. preferably, stretching said melt extrudate to form a stretched extrudate; and
  iii) cutting said stretched extrudate to form particulates.

Viewed from a further aspect, the present invention provides a dosage form as hereinbefore described for use in medicine (e.g. for use in the treatment or management of pain).

Viewed from a further aspect the present invention provides particulates as hereinbefore described for use in medicine (e.g. for use in the treatment or management of pain).

Viewed from a further aspect, the present invention provides use of melt-extruded particulates comprising a drug (e.g. a drug susceptible to abuse) and a matrix material in the manufacture of a dosage form as hereinbefore described for the treatment of pain.

Alternatively viewed, the invention also provides a method of treating a subject in need of pain relief comprising administering to said subject a dosage form comprising a drug (e.g. a drug susceptible to abuse) as hereinbefore described.

In preferred embodiments of the present invention, the dosage form is tamper resistant.

In further preferred embodiments of the present invention, the drug is a drug susceptible to abuse.

In further preferred embodiments of the present invention, the particulates present in the dosage form are microparticulates.

DETAILED DESCRIPTION OF THE INVENTION

As used herein, the term "dosage form" refers to a pharmaceutical entity that is comprised of a drug and which is actually administered to, or taken by, a patient. A representative example of a dosage form is a tablet. A capsule is another dosage form. Preferred dosage forms of the invention are tablets. Preferred dosage forms are designed for oral administration.

As used herein, the term "tamper resistant" refers to dosage forms that are resistant to alcohol extraction. The dosage forms can therefore impede abuse. Preferred tamper resistant dosage forms of the present invention are resistant to alcohol extraction and to crushing.

Preferred dosage forms of the invention are those wherein the amount of drug released from the dosage form at 0.5 hour when measured in a USP Apparatus 1 (basket) at 100 rpm in 900 ml simulated gastric fluid without enzymes (SGF) with 40% ethanol at 37° C., is within ±20% (e.g. within ±10%, still more preferably within ±5%) of the amount of drug released from the dosage form at 0.5 hour when measured in a USP Apparatus 1 (basket) at 100 rpm in 900 ml simulated gastric fluid without enzymes (SGF) with 0% ethanol at 37° C. In particularly preferred dosage forms, the amount of drug released from the dosage form at 0.5 hour when measured according to the above-mentioned test in SGF with 40% ethanol is less than or approximately equal to the amount of drug released in SGF with 0% ethanol. Still more preferably the amount of drug released at 0.5 hour when measured according to the above-mentioned test in SGF with 40% ethanol is 90% or less, more preferably 80% or less, e.g. 70% or less, of the amount of drug released in SGF with 0% ethanol.

In particularly preferred dosage forms of the invention the dosage form can be flattened (e.g. with hammer strikes) without breaking to a thickness of less than about 60%, preferably to a thickness of less than about 50%, still more preferably to a thickness of less than about 40%, of the thickness of the dosage form before flattening. Particularly preferred dosage forms can be flattened (e.g. with hammer strikes) without breaking to a thickness of from about 10% to about 99%, from about 20% to about 80%, or from about 40% to about 60% of the thickness of the dosage form prior to flattening. Particularly preferred dosage forms of the invention have a breaking strength of at least 350 Newtons, preferably 500 Newtons, e.g. 400-495 Newtons, as tested according to the procedure set out in the examples herein.

The dosage forms of the present invention comprise particulates as a discontinuous phase. As used herein the term "particulate" is used to refer to a discrete mass of material that is solid, e.g. at 20° C. or at room temperature or ambient temperature. Preferably a particulate is solid at 20° C.

The particulates present in the dosage forms of the present invention are prepared from a melt extrudate comprising a drug, and more preferably, from a stretched, melt extrudate comprising a drug. Thus the particulates present in the dosage forms of the present invention are preferably prepared by melt extruding a composition comprising a drug to form a melt extrudate, stretching said melt extrudate and cutting the stretched extrudate. The preferred particulates present as the discontinuous phase of the dosage forms of the present invention are therefore different from conventional multiparticulates, which generally have dimensions of about 1 mm (length)×1 mm (diameter), as they are formed from stretched melt extrudate and thus have a significantly smaller diameter than conventional multiparticulates. As such they may be likened to or considered as fibres. Advantageously, this enhances crush resistance and enables the particulates to be incorporated into a matrix. Preferably, the particulates present as the discontinuous phase of the dosage forms are also unaffected by compression forces.

Preferred particulates present in the dosage forms of the present invention are microparticulates. As used herein, the term "microparticulates" is used to refer to particulates having an average length and average diameter of 1000 μm or less. The "length" of particulates is the dimension of the particulates that is parallel to the direction of extrusion. The "diameter" of particulates is the largest dimension that is perpendicular to the direction of extrusion.

Preferred particulates present in the dosage forms of the present invention are generally cylindrical in shape. The diameter of such particulates is therefore the diameter of their circular cross section.

Particularly preferred particulates, e.g. microparticulates have an average diameter of less than about 1000 μm, more preferably an average diameter of less than about 800 μm, still more preferably an average diameter of less than about 650 μm. Especially preferred particulates have an average diameter of less than 700 μm, particularly less than 600 μm, still more particularly less than 500 μm, e.g. less than 400 μm. Particularly preferred particulates therefore have an average diameter in the range 200-1000 μm, more preferably 400-800 μm, still more preferably 450-700 μm, yet more preferably 500-650 μm, e.g. about 500-600 μm. Further preferred particulates have an average diameter of between about 300 μm and about 400 μm, of between about 400 μm and 500 μm, or of between about 500 μm and 600 μm. The smaller diameter of the particulates, e.g. microparticulates of the present invention compared to conventional multiparticulates is preferably achieved by stretching the melt extrudate prior to its pelletisation. The minimum average diameter of the particulates, e.g. microparticulates may therefore be largely determined by how far the extrudate can be reliably stretched without breaking and might be, e.g. about 500 μm, about 400 μm, about 300 μm or about 200 μm, depending on the composition of the melt extrudate.

Preferred particulates that are present in the dosage forms of the present invention have an average length of less than about 1000 μm, preferably an average length of less than about 800 μm, still more preferably an average length of less than about 650 μm, e.g. a length of about 600 μm, about 500 μm, about 400 μm or about 300 μm. Especially preferred particulates have an average length of less than 700 μm, particularly less than 650 μm, still more particularly less than 550 μm, e.g. less than 450 μm. Particularly preferred particulates therefore have an average length in the range 200-1000 μm, more preferably 400-800 μm, still more preferably 450-700 μm, yet more preferably 500-650 μm, e.g. about 500-600 μm. The minimum average length of the microparticulates is determined by the cutting step and may be, e.g. 500 μm, 400 μm, 300 μm or 200 μm.

The size of particulates may be determined by any conventional procedure known in the art, e.g. laser light scattering, sieve analysis, light microscopy or image analysis.

The particulates present in the dosage forms of the present invention are crush resistant. Thus, preferably the particulates can be flattened (e.g. with hammer strikes) without breaking to a thickness of less than about 60%, preferably to a thickness of less than about 50%, still more preferably to a thickness of less than about 40%, of the thickness of the particulate before flattening. Particularly preferred particulates can be flattened (e.g. with hammer strikes) without breaking to a thickness of from about 10% to about 99%, from about 20% to about 80%, or from about 40% to about 60% of the thickness of the particulate prior to flattening. Some particulates for use in the invention may have a breaking strength of at least 350 Newtons, preferably 500 Newtons, e.g. 400-495 Newtons, as tested according to the procedure set out in the examples herein.

The particulates present in the dosage forms of the present invention preferably comprise a drug susceptible to abuse. The drug susceptible to abuse is preferably an opioid agonist, a tranquilizer, a CNS depressant, a CNS stimulant or a sedative hypnotic. Particularly preferably the drug susceptible to abuse is an opioid agonist.

In particularly preferred dosage forms of the present invention, the drug is an opioid agonist selected from the group consisting of oxycodone, oxymorphone, hydrocodone, hydromorphone, morphine, codeine, buprenorphine, fentanyl, tramadol, tapentadol and pharmaceutically acceptable salts thereof. Still more preferably the drug present is an opioid agonist selected from the group consisting of oxycodone, oxymorphone, hydrocodone, hydromorphone, morphine, codeine and pharmaceutically acceptable salts thereof. In some embodiments of the present invention, the preferred opioid agonist is oxycodone. In other preferred embodiments, the preferred opioid agonist is hydromorphone. The skilled man will readily determine what are suitable pharmaceutically acceptable salts.

Pharmaceutically acceptable salts include, but are not limited to, metal salts such as sodium salt, potassium salt and cesium salt; alkaline earth metals such as calcium salt and magnesium salt; organic amine salts such as triethylamine salt, pyridine salt, picoline salt, ethanolamine salt, triethanolamine salt, dicyclohexylamine salt and N,N'-dibenzylethylenediamine salt; inorganic acid salts such as hydrochloride, hydrobromide, sulfate and phosphate; organic acid salts such as formate, acetate, trifluoroacetate, maleate and tartrate; sulfonates such as methanesulfonate, benzenesulfonate and p-toluenesulfonate; amino acid salts such as arginate, asparginate and glutamate. Inorganic acid salts are generally preferred.

Oxycodone hydrochloride and hydromorphone hydrochloride are preferred opioid agonists.

The drug that is included in the preparation of the dosage forms of the present invention preferably has an average particle size of less than 500 microns, still more preferably less than 300 microns, yet more preferably less than 200 or 100 microns. There is no lower limit on the average particle size and it may be, for example, 50 microns. The particle size of drugs may be determined by any technique conventional in the art, e.g. laser light scattering, sieve analysis, light microscopy or image analysis. Generally speaking it is preferable that the largest dimension of the drug particle be less than the size of the particulates (e.g. less than the smallest dimension of the particulates). It is also believed to be generally advantageous to utilise drug particles and non-melting and/or non-softening excipients having a particle size that is less than half the diameter of the stretched melt extrudate. This serves to ensure that the particulates comprising the drug forms a discontinuous phase in a continuous matrix. When this is achieved the extrudate can be stretched with little risk of breakage.

The particulates present in the dosage forms of the present invention preferably comprise 3 to 50% wt of drug, more preferably 5 to 40% wt of drug, still more preferably 7.5 to 35% wt of drug, e.g. 10 to 20% wt of drug, wherein the % wt is based on the total weight of a particulate.

The dosage forms of the present invention may also comprise one or more additional active ingredients. The additional active may be a drug susceptible to abuse or another pharmaceutical. Additional active ingredients may be present within the above-described particulates ("intragranular") or within the matrix ("extragranular"). Where an additional active ingredient is present intragranularly, it may be present either in combination with one or more active ingredients within the same particulates or in a discreet population of particulates alone and separate from any other active ingredient present in the dosage form.

Preferred particulates present in the dosage forms of the present invention are those having a suitable tensile strength as determined by a test method currently accepted in the art. Further preferred particulates are those having a Youngs Modulus as determined by a test method of the art. Still further preferred particulates are those having an acceptable elongation at break.

The particulates present in the dosage forms of the present invention preferably comprise a polymer that imparts crush resistance, particularly preferably a rubbery polymer or a polymer with plastic properties. The presence of this polymer means that if a dosage form is crushed by an abuser, the drug is not released from the particulates. Furthermore, due to the sufficiently small size of the particulates present in the matrix, they cannot be separated from the crushed matrix by the abuser. Preferred polymers that impart crush resistance include Eudragit® NE or NM polymer, or a polymer with plastic properties, such as a Eudragit® RS or RL polymer.

In preferred dosage forms of the invention, the polymer conferring crush resistance, e.g. rubbery polymer, is an acrylic polymer, a methacrylic polymer or mixtures thereof. Thus, the dosage forms of the present invention preferably comprise a polymer selected from an acrylic polymer, a methacrylic polymer or mixtures thereof. In addition to increasing crush resistance, these polymers also ease melt extrusion as well as help to control the rate of release of the drug from the particulates.

Representative examples of acrylic and methacrylic polymers include acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

Particularly preferably the particulates present in the dosage form of the present invention comprise a copolymer of acrylic acid alkyl esters, methacrylic acid alkyl esters and mixtures thereof. Preferred alkyl esters are methyl and ethyl esters. Particularly preferably the copolymer is of ethyl acrylate and methyl methacrylate.

The polymer conferring crush resistance, e.g. rubbery polymer, may be neutral (i.e. carry no charge) or may be charged. In neutral polymers the side chains (e.g. the alkyl group of alkyl ester side chains) are typically non-functionalised. In charged polymers, the side chain (e.g. the alkyl group of alkyl ester side chains) is typically functionalised with, e.g. a quaternary ammonium group such as trimethylammonio. Trimethylammonio groups are preferably present as salts and tend to render the polymers water permeable. Preferably the polymer conferring crush resistance is neutral (i.e. not charged).

Particularly preferably the polymer conferring crush resistance, e.g. rubbery polymer such as a copolymer of ethyl acrylate and methyl methacrylate, has an average molecular weight in the range 50,000 to 200,000, more preferably 60,000 to 150,000, e.g. 70,000 to 100,000. Average molecular weight is number average molecular weight.

Acrylic and methacrylic polymers for use in the particulates present in the dosage forms of the invention are commercially available, for example, from Evonik. Representative examples of suitable polymers include those sold under the tradename Eudragit, especially Eudragit® RL 100, Eudragit® RL PO, Eudragit® RS 100, Eudragit® RS PO, Eudragit® NE 40 D, Eudragit® NE 30 D. Eudragit® NE 40 D, Eudragit® NE 30 D and Eudragit® NM 30 D, which are neutral copolymers of ethyl acrylate and methyl methacrylate having an average molecular weight of about 150,000, are especially preferred.

The particulates present in the dosage forms of the present invention preferably comprise 10 to 50% wt, more preferably 20 to 40% wt, still more preferably 25 to 35% wt of polymer conferring crush resistance, e.g. rubbery polymer such as an acrylic polymer, a methacrylic polymer or mixture thereof, based on the total weight of a particulate.

The drug may be soluble in the polymer conferring crush resistance, e.g. rubbery polymer such as acrylic polymer, methacrylic polymer or mixture thereof. Preferably, however, the drug is not soluble therein.

The particulates present in the dosage forms of the present invention preferably comprise a rate controlling or modifying agent. As used herein, the term rate controlling or modifying agent is used to refer to a constituent of the particulates that is included for the purpose of impacting upon the rate of release of drug from the particulates. Preferred rate controlling or modifying agents for use in the particulates are those providing controlled, especially sustained, release.

Preferred rate controlling or modifying agents for use in the present invention are hydrophobic materials, especially hydrophobic polymers. Further preferred rate controlling or modifying agents are water insoluble materials, especially water insoluble polymers.

The rate controlling or modifying agent may be, but need not necessarily be, a polymer which confers crush resistance.

Particularly preferred rate controlling or modifying agents for use in the particulates are alkylcelluloses. These include natural and synthetic alkylcelluloses. Both water-soluble and water-insoluble cellulose derivatives are also suitable. Representative examples of alkylcelluloses and hydroxy alkyl celluloses include water soluble methylcellulose, hydroxy propyl cellulose and hydroxylpropyl methylcellulose. An example of a water insoluble alkylcellylose is ethylcellulose. A particularly preferred alkylcellulose for use as the rate controlling or modifying agent in the particulates present in the dosage forms of the invention is ethylcellulose.

Suitable alkyl celluloses for use in the particulates are commercially available. Examples of commercially available alkylcelluloses that may be present include ethyl cellulose N10 and N45 as well as the aqueous dispersion, Surerelease E-7-1940. Ethyl cellulose N10 and N45 are particularly preferred. They are available from numerous suppliers. The alkyl cellulose may be in the form of granules, powder or fine powder. All forms are commercially available.

Other rate controlling or modifying agents which may be suitable for employment in the particulates of the dosage forms of the present invention include insoluble hydrophilic wicking agents, such as microcrystalline cellulose, croscarmellose sodium, crospovidone and sodium starch glycolate;

gelling agents which hydrate to form gels to control the movement of water, such as high molecular weight grade (high viscosity) hydroxypropylmethyl cellulose (HPMC), polyethylene oxide, pectin, locust bean gum and xanthan gum; high molecular weight polyethylene glycols, such as PEG 6000; and water permeable ammonium methacrylate (also referred to as ammonio methacrylate) copolymers, such as Eudragit® RL PO.

The particulates present in the dosage forms of the present invention preferably comprise 20 to 50% wt of rate controlling or modifying agent, more preferably 25 to 45% wt of rate controlling or modifying agent, still more preferably 30 to 40% wt of rate controlling or modifying agent based on the total weight of a particulate.

Preferred particulates present in the dosage forms of the invention may also comprise a lubricant. Lubricants are processing aids that reduce friction between the polymer mixture or blend and, e.g., the internal surfaces the extruder. Representative examples of lubricants include stearic acid, glyceryl behenate (e.g. in the form of glyceryl dibehenate), magnesium stearate, calcium stearate, talc and silicone dioxide (fused silica). The presence of the lubricant in the extrusion mixture improves blending, kneading and conveying, and reduced adhesion forces. Smooth lubricated extrusion at low to moderate temperatures improves batch to batch reproducibilty and reduces the strain on both the product and manufacturing equipment. Glyceryl dibehenate is a preferred lubricant for use in the particulates.

The amount of lubricant present in the particulates is preferably in the range 1 to 25% wt, more preferably 2 to 15% wt, still more preferably 3 to 10% wt based on the total weight of a particulate.

Preferred particulates present in the dosage forms of the invention also comprise a plasticiser. Plasticisers facilitate extrusion as well as reduce cohesion by providing internal lubrication of any polymers present therein. Representative examples of plasticisers include water-insoluble solids (e.g. cetyl alcohol, stearyl alcohol and cetostearyl alcohol), water-soluble solids (e.g. sorbitol, sucrose, polyethylene glycol), and liquids (e.g. dibutyl sebacate, tributyl citrate, acetyltributyl citrate, triethyl citrate, acetyltriethyl citrate, triacetin, dibutylphthalate, diethylphthalate, propylene glycol and polysorbate 80). A preferred solid plasticiser is stearyl alcohol. Liquid plasticisers are also preferred. Triethyl citrate is a preferred liquid plasticiser.

The amount of plasticiser present in the dosage forms of the present invention is preferably in the range 1 to 30% wt, more preferably 5 to 20% wt, still more preferably 10 to 15% wt, based on the total weight of a particulate.

Plasticisers can sometimes act as a lubricant, and lubricants can sometimes act as a plasticiser.

When the particulates present in the dosage forms of the present invention comprise an opioid agonist, the dosage form may also comprise an opioid antagonist. Any conventional opioid antagonist may be present, e.g. naltrexone or naloxone or their pharmaceutically acceptable salts. Naloxone, including its salts, is particularly preferred. The opioid antagonist may be present within the particulates or within the matrix. Alternatively opioid antagonist may be provided in separate particulates to the above-described drugs. The preferred composition of such particulates is the same as that described for drug-containing particulates.

Particularly preferred dosage forms of the present invention comprise naloxone, especially naloxone hydrochloride, and particulates comprising an opioid agonist selected from oxycodone or one of its pharmaceutically acceptable salts and hydromorphone or one of its pharmaceutically acceptable salts. Particularly preferred opioid agonists are oxycodone hydrochloride and hydromorphone hydrochloride.

The ratio of opioid agonist to opioid antagonist in the dosage forms of the present invention is preferably 1:1 to 3:1 by weight, for example, about 2:1 by weight. For example, when the opioid agonist is hydromorphone HCl and the opioid antagonist is naloxone HCl, the agonist:antagonist ratio may be 1:1 to 3:1 by weight, e.g. about 2:1 by weight. When the opioid agonist is oxycodone HCl and the opioid antagonist is naloxone HCl, the agonist:antagonist ratio may be 1:1 to 3:1 by weight, preferably about 2:1 by weight.

When opioid antagonist is present in the dosage forms of the invention, the total amount of opioid agonist and opioid antagonist present in the particulates is preferably in the range 5 to 40% wt, more preferably 10 to 30% wt, still more preferably 20 to 25% wt, based on the total weight of a particulate. When the opioid agonist is hydromorphone or a salt thereof (e.g. the HCl salt) and an antagonist is present (e.g. naloxone HCl) the amount of hydromorphone or salt thereof present in the dosage form is preferably 2-80 mg or 5-80 mg, e.g. 5, 10, 20, 40 or 80 mg, still more preferably the amount of hydromorphone or salt thereof is 2-32 mg, e.g. 2, 4, 6, 8, 10, 12, 14, 16, 18, 20, 24, 28 or 32 mg. When the opioid agonist is oxycodone or a salt thereof (e.g. the HCl salt) and an antagonist is present (e.g. naloxone HCl) the amount of oxycodone or salt thereof present in the dosage form is preferably 2-32 mg or 5-80 mg, e.g. 2, 4, 8, 16 or 32 mg, still more preferably the amount of oxycodone or salt thereof is 5-80 mg, e.g. 5, 10, 20, 30, 40, 50, 60, 70 or 80 mg.

Suitable percentage amounts for each of the above-described preferred constituents of the particulates present in the dosage forms of the present invention are given in the following table, based on the total weight of a particulate. The table is intended to disclose any of the ranges indicated in combination with any of the other preferred ranges.

|  | Typical range % | Preferred range % | More preferred range % |
| --- | --- | --- | --- |
| Opioid agonist | 3 to 50 | 5 to 40 | 7.5 to 35 |
| Rubbery polymer | 10 to 50 | 20 to 40 | 25 to 35 |
| Rate controlling or modifying agent | 20 to 50 | 25 to 45 | 30 to 40 |
| Lubricant | 1 to 25 | 2 to 15 | 3 to 10 |
| Plasticiser | 1 to 30 | 5 to 20 | 10 to 15 |

The particulates present in the dosage forms of the present invention may additionally contain other excipients that are conventional in the art, e.g. diluents, binders, granulating aids, colourants, flavourants, glidants and other release-modifying agents. The skilled man will readily be able to determine appropriate further excipients as well as the quantities of each of these excipients. Specific examples of pharmaceutically acceptable carriers and excipients that may be used to formulate the dosage forms of the invention are described in the Handbook of Pharmaceutical Excipients, American Pharmaceutical Association (1986), the contents of which are incorporated herein.

Lactose, glucose or saccharose, starches and their hydrolysates, microcrystalline cellulose, cellatose, sugar alcohols such as sorbitol or mannitol, polysoluble calcium salts like calciumhydrogenphosphate, dicalcium- or tricalciumphosphate may be used as fillers. Povidone may be used as granulating aid. Highly-dispersed silica, talcum, corn starch, magnesium oxide and magnesium or calcium stearate may preferably be used as flowing agents.

Particularly preferred particulates present in the dosage forms of the present invention comprise oxycodone or hydromorphone, preferably as their hydrochloride salts, an ethyl acrylate and methyl methacrylate copolymer, preferably Eudragit® NE 30 D or NE 40 D, ethyl cellulose as rate controlling or modifying agent, stearyl alcohol and/or triethyl citrate as plasticiser, glyceryl dibehenate as lubricant, and optionally opioid antagonist. If an opioid antagonist is present, it is preferably naloxone, especially in the form of its hydrochloride salt.

The particulates present in the dosage forms of the present invention are preferably prepared by mixing the constituents, melt-extruding the mixture and then stretching and cutting the extrudate, e.g. to a predetermined diameter and length. Mixing may be achieved by any conventional means, e.g. blending and/or granulation, that achieves homogeneity. In a preferred method, the mixing of the constituents is achieved by granulation. The granulate is preferably dried. The granulate can then be extruded, stretched and cut as described. For example, the drug can be granulated together with the other constituents to produce drug-containing granules, the granules then dried, and the dried granules extruded and cut. Alternatively, the constituents minus drug can be granulated to produce placebo granules, the placebo granules dried before then being dry blended with drug, and the resulting dry blend extruded and cut. The latter is a preferred method for producing particulates containing water-sensitive active agents, e.g. hydromorphone or a pharmaceutically acceptable salt thereof as drug.

In a particularly preferred method, a liquid plasticiser is mixed with a rate controlling or modifying polymer (e.g. ethylcellulose) in an amount of 5-25% wt (based on the weight of the rate releasing polymer) and allowed to stand for, e.g., 5 to 12 hours. This allows the plasticiser to penetrate deep into the polymer structure lowering its glass transition temperature ($T_g$) and ultimately increasing the crush resistance of the rate controlling or modifying polymer. The plasticised rate controlling or modifying polymer is then mixed, e.g. granulated, with the other constituents, e.g. opioid agonist, polymer conferring crush resistance (e.g. rubbery polymer and/or polymer with plastic properties), lubricant and plasticiser. Mixing may be carried out using any conventional mixer.

Extrusion may be carried out using any conventional extrusion equipment, e.g. a melt extruder, but preferably a twin screw extruder, which may have co-rotating or counter-rotating screws, is used. Typically, the mixture (e.g. as a powder or dry granules) is fed by a feeder into the first segment of the barrel, usually at relatively low temperature (e.g. 10-20° C.), to ensure constant flow to the higher temperature barrel segments. The feeder provides a uniform current of the blend to the extruder. Consistency is desirable as irregular and variable feeding rates can produce particulates with varying physical properties, such as density and porosity.

The preferred extruder is designed with twin screws, preferably counter-rotating screws, for the task of conveying, blending, compressing, heating and softening the mixture. Depending on the choice of the components of the blend and the extrusion conditions, it may be that the blend will melt as well as soften. The screws which perform a significant part of this extrusion process are built of different smaller elements chosen from a variety of screw elements and kneader elements. Mixing and kneading time can be significantly altered by changing the type, length and configuration of the screw elements and possibly kneader elements. Short residence times and moderate to low shear forces contribute to safe processing and stable product even with heat sensitive drugs. Examples of suitable extruders include those manufactured by Leistritz, Brabender, Randcastle, and Kurimoto Co. Ltd.

Screw rotating speeds may play a part in the quality of the particulates produced. High rotation speeds without appropriate compensation of the blend feed rate may produce high porosity particulates with a variable drug release rate. On the other hand slow screw rotation would induce unnecessary long residence times. A vacuum connected to the extruder barrel is desirable to remove trapped air within the softened blend and thus produce dense, low porosity particulates.

In addition to the screw speed, the other main influential parameters are the screw torque, individual barrel temperature, and extrusion head pressure and temperature. Preferably, extrusion is carried out at a temperature of 100° C. or less, e.g. 80-100° C.

The extrusion head is typically designed to produce multiple strands of fixed diameter. The number, shape and diameter of the orifices can be changed to suit a predetermined specification. Typically, however, the diameter of the extrudate is 1.0-1.2 mm, i.e. the same as that of conventional extrudate. An advantage of a preferred embodiment of the present invention is therefore that conventional extrusion equipment can be used in the same way as during the preparation of conventional multiparticulates. This means that there is no need to reduce the size of the die holes (which could result in an increased likelihood of blockages) or to increase the pressure levels required to achieve the extrusion.

Extrusion is also a well-established production process in pharmaceutical technology and is well known to the person skilled in the art. The person skilled in the art is well aware that during the extrusion process, various parameters, such as the feeding rate, the screw speed, the heating temperature of the different extruder zones (if available), the water content, etc. may be varied in order to produce products of the desired characteristics.

The aforementioned parameters will depend on the specific type of extruder used. During extrusion the temperature of the heating zones, in which the components of the inventive formulation melt, may be between 40 to 120° C., preferably between 50 to 100° C., more preferably between 50 to 90° C., even more preferably between 50 to 70° C. and most preferably between 50 to 65° C., particularly if counter-rotating twin screw extruders are used. The person skilled in the art is well aware that not every heating zone has to be heated. Particularly behind the feeder where the components are mixed, cooling at around 25° C. may be necessary. The screw speed may vary between 50 to 500 revolutions per minute (rpm), preferably between 100 to 250 rpm, more preferably between 100 to 200 rpm and most preferably around 150 rpm, particularly if counter-rotating twin screw extruders are used. The geometry and the diameter of the nozzle may be selected as required. The diameter of the nozzle of commonly used extruders typically is between 1 to 10 mm, preferably between 2 to 8 mm and most preferably between 3 to 5 mm. The ratio of length versus diameter of the screw of extruders that may be used for production of the dosage forms herein described is typically around 40:1.

Generally, the temperatures of the heating zones have to be selected such that no temperatures develop that may destroy the pharmaceutically active compounds. The feeding rate and screw speed will be selected such that the pharmaceutically active compounds are released from the preparations produced by extrusion in a sustained, independent and invariant manner. If e.g. the feeding rate is increased, the screw speed may have to be increased correspondingly to ensure the same retardation.

The person skilled in the art knows that all the aforementioned parameters depend on the specific production conditions (extruder type, screw geometry, number of components etc.) and may have to be adapted such that the extrudate produced has the desired properties.

Preferably the melt extrudate is then stretched. This is preferably carried out whilst the extrudate is still flexible. Preferably, stretching is carried out using the conveyor belt that transports the extrudate to the pelletiser and/or the nip rollers of the pelletiser. Particularly preferably, the conveyor belt speed and nip rollers speed are coordinated and adjusted to achieve the desired stretching. Typically the conveyor belt and/or nip rollers are set to process the extrudate at a faster rate than it emerges from the extruder. The skilled man will, however, be able to readily determine appropriate settings for the extruder, conveyor belt, nip rollers etc in order to achieve the desired stretching.

During the process of stretching, the diameter of the melt extrudate is decreased and the length of the extrudate is correspondingly increased. Preferably, the stretching reduces the diameter of the melt extrudate to 80-30% of its original diameter, more preferably 75-40%, still more preferably 70-45%, yet more preferably 60-50%, e.g. about 50% of its original diameter. The maximum amount by which the melt extrudate can be stretched might be that which reduces the diameter of the extrudate to a diameter in the range of about 40% to about 30% (e.g. 30%) of the original diameter, depending on the composition of the melt extrudate and/or on the particle size of the drug present therein.

Particularly preferably the average diameter of the stretched melt extrudate is less than about 1000 µm, more preferably less than about 800 µm, still more preferably less than about 650 µm, e.g. less than 600 or 500 µm, and even more preferably still, less than about 450 µm, e.g between about 300 µm and about 400 µm. The minimum average diameter of the particulates is largely determined by how far the extrudate can be reliably stretched without breaking and might be, e.g. about 500 µm, 400 µm, 300 µm or 200 µm. Again this depends on the precise composition of the extrudate. The average diameter of the stretched melt extrudate is therefore preferably in the range 200-1000 µm, more preferably 400-800 µm, still more preferably 450-700 µm, yet more preferably 500-650 µm, e.g. about 500-600 µm. In other preferred embodiments, the average diameter of the stretched melt extrudate is in the range 300-600 µm, e.g. 400-500 µm.

The diameter of the stretched melt extrudate is preferably consistent over time. Thus, the aforementioned average particle diameters are preferably achieved ±20%, and more preferably ±10%, e.g. ±5%.

Laser diameter measurement may optionally be employed between the conveyor belt and the pelletiser to continuously monitor the diameter of extrudate. The information provided by the monitoring system can be used to guide adjustment of the conveyor belt speed and/or nip roller speed. Laser diameter measurement may also be used to determine the average diameter of extrudate.

To produce the particulates present in the dosage form of the present invention, the stretched melt extrudate is cut. Cutting may be carried out by any conventional procedure known in the art. For instance the stretched extrudate may be fed into a pelletiser by nip rolls. The pelletiser then cuts the fed extrudate, for instance using a rotary knife cutter, to a pre-determined length, e.g. to an average length of less than about 1000 µm, preferably an average length of less than about 800 µm, still more preferably an average length of less than about 650 µm e.g. a length of about 600 µm or 500 µm. In other preferred embodiments, the fed extrudate is cut to an average length of between about 300 and 600 µm, e.g. about 400 µm, 450 µm or 500 µm. The feeding rate, e.g. the conveyor belt speed, of the melt extrudate and the pelletiser cutter speed largely determine the length of the particulates. The minimum average length of the particulates may be, e.g. 400 µm to 200 µm (e.g. 200 µm). The average length of the particulates is therefore preferably in the range 200-1000 µm, e.g. about 300 µm, about 400 µm or about 500 µm, more preferably 400-800 µm, e.g. about 400-500 µm, still more preferably 450-700 µm, e.g. about 450-600 µm, yet more preferably 500-650 µm, e.g. about 500-600 µm.

In the dosage forms of the present invention, the above-described particulates are incorporated into a matrix. As used herein, the term "matrix" is used to refer to a continuous phase present in the dosage form. The matrix of the dosage forms of the present invention preferably comprises one or more gel-forming agents and/or a silicone. Preferred silicones are described below.

Preferably the matrix of the dosage forms comprises one or more gel-forming agents. Preferred gel-forming agents are polymers. Average molecular weights of polymers present in the matrix are number averages, unless otherwise specified.

As used herein the term "gel-forming agent" is used to refer to a compound that, upon contact with a solvent (e.g. water), absorbs the solvent and swells, thereby forming a viscous or semi-viscous substance. This substance may moderate drug release from the embedded particulates in both aqueous and aqueous alcoholic media. Upon full hydration, a thick viscous solution or dispersion is typically produced that significantly reduces and/or minimizes the amount of free solvent which can contain an amount of solublised drug, and which can be drawn into a syringe. The gel that is formed may also reduce the overall amount of drug extractable with the solvent by entrapping the drug within a gel structure. Thus the gel-forming agent may play an important role in conferring tamper resistance to the dosage forms of the present invention.

Preferred gel-forming agents that may be used in the dosage forms of the present invention include pharmaceutically acceptable polymers, typically hydrophilic polymers, such as hydrogels. Preferred polymers for use as a gel-forming agent exhibit a high degree of viscosity upon contact with a suitable solvent. The high viscosity can enhance the formation of highly viscous gels when attempts are made by an abuser to crush and dissolve the contents of a dosage form in an aqueous and/or aqueous alcoholic vehicle and inject it intravenously.

Representative examples of polymers that may be used as a gel-forming agent include polyethylene oxide, polyvinyl alcohol, hydroxypropylmethyl cellulose, carbomers, poly (uronic) acids and mixtures thereof. Preferred features of each of these polymers are described below.

Particularly preferred silicones and gel-forming agents (e.g. polymers) for use in the dosage forms of the present invention are those that are curable. As used herein, the term curable is used to refer to agents, typically polymers, that can undergo cross-linking, e.g. by heating. The cross-linking that is introduced during the curing process serves to harden or toughen the agent, e.g. polymer, and thereby impart crush resistance to the dosage form. Such dosage forms are particularly preferred as they comprise two mechanisms of providing crush resistance, namely by way of the cured matrix as well as the particulates.

Representative examples of polymers that may be used as curable agents include polyethylene oxide, polyvinyl alcohol, carbomers, poly(uronic) acids, silicones and mixtures thereof. A particularly preferred curable, gel-forming agent is polyethylene oxide. Another preferred curable agent is silicone.

Polyethylene Oxide

The matrix of the dosage forms of the present invention may comprise a polyethylene oxide (PEO). The PEO present in the dosage forms of the present invention preferably is a homopolymer. Particularly preferably, the PEO is a homopolymer having repeating oxyethylene groups, i.e. —(O—$CH_2$—$CH_2$)$_n$— wherein n may be from about 2,000 to about 180,000.

Particularly preferably, the PEO has an average molecular weight of at least about 1,000,000, e.g. based on rheological measurements. Still more preferably the PEO has an average molecular weight of about 2,000,000 to about 7,000,000, e.g. about 3,000,000 to about 4,000,000.

Preferably, the PEO has a viscosity of 400 to 5,000 cps as a 2% aqueous solution at 25° C., more preferably the PEO has a viscosity of 400 to 800 cps as a 2% aqueous solution at 25° C.; yet more preferably a viscosity of 2,000 to 4,000 cps as a 2% aqueous solution at 25° C. The PEO may also preferably have a viscosity of 1,500 to 12,000 cps as a 1% aqueous solution at 25° C., more preferably a viscosity of 1,650 to 5,500 cps as a 1% aqueous solution at 25° C., still more preferably a viscosity of 5,500 to 7,500 cps as a 1% aqueous solution at 25° C. and yet more preferably a viscosity of 7,500 to 10,000 cps as a 1% aqueous solution at 25° C.

Particularly preferably, the PEO present in the dosage forms of the invention is a polymer having an average molecular weight and viscosity as described in the Table below. For instance, a preferred PEO for use in the dosage forms of the present invention has an average molecular weight of 4,000,000 and a viscosity of 1650-5500 cps as a 1% aqueous solution at 25° C. Another preferred PEO for use in the dosage forms of the present invention has an average molecular weight of 5,000,000 and a viscosity of 5,550-7,500 cps as a 1% aqueous solution at 25° C. Yet another preferred PEO for use in the dosage forms of the present invention has an average molecular weight of 7,000,000 and a viscosity of 7,500-10,000 cps as a 1% aqueous solution at 25° C.

|  | Viscosity range at 25° C. (CPS) | |
| --- | --- | --- |
| Molecular weight | 2% solution | 1% solution |
| 1,000,000 | 400-800 |  |
| 2,000,000 | 2,000-4,000 |  |
| 4,000,000 |  | 1,650-5,500 |
| 5,000,000 |  | 5,500-7,500 |
| 7,000,000 |  | 7,500-10,000 |

In some embodiments of the present invention, the matrix may comprise a mixture of PEO having different molecular weights. It may, for example, be advantageous in some dosage forms to include PEO having an average molecular weight, based on rheological measurements, of at least 1,000,000 (e.g. 2,000,000-7,000,000 as described above) as well as PEO having an average molecular weight, based on rheological measurements, of less than 1,000,000 (e.g. 200,000-800,000). Such dosage forms may possess the advantageous features of crush resistance and modified and/or controlled, e.g. sustained, release of the drug.

PEO that is suitable for use in the dosage forms of the invention is commercially available from Dow. For example, Polyox WSR N-12K, Polyox N-60K, Polyox WSR 301NF or Polyox WSR 303NF may be used in the dosage forms of the present invention.

Polyvinyl Alcohol

The matrix of the dosage forms of the present invention may comprise a polyvinyl alcohol. The polyvinyl alcohol preferably has an average molecular weight of about 20,000 to about 200,000. The viscosity of the polyvinyl alcohol is preferably from about 4 to about 65 cps as a 4% aqueous solution at 25° C.

The polyvinyl alcohol used in the matrix is preferably a water-soluble polymer. Preferred polyvinyl alcohol has the formula —($C_2H_4O$)$_n$— where n can range from about 500 to about 5,000. Representative examples of commercially available polyvinyl alcohol polymers that may be used in the matrix of the dosage forms of the present invention include PVA, USP, available from Spectrum Chemical Manufacturing Corporation.

Hydroxypropyl Methylcellulose

The matrix of the dosage forms of the present invention may comprise a hydroxypropyl methylcellulose polymer. The viscosity of the hydroxypropyl methylcellulose is preferably about 1,000 to about 150,000 cps, more preferably about 3,000 to 120,000 cps, e.g. 3,000-5,600 cps, 11,250-21,000 cps or 80,000-120,000 cps, as a 2% aqueous solution at 25° C.

The hydroxypropyl methylcellulose present in the matrix of the dosage forms of the present invention is preferably a water-soluble polymer. Examples of commercially available hydroxypropyl methylcellulose polymers that may be used in the dosage forms include Methocel™ K4M, Methocel™ K15M and Methocel™ K100M available from The Dow Chemical Company.

Carbomers

The matrix of the dosage forms of the present invention may comprise a carbomer. The carbomers preferably have a molecular weight ranging from 700,000 to about 4,000,000,000. The viscosity of the carbomer is preferably in the range from about 4000 to about 39,400 cps as a 1% aqueous solution at 25° C. at neutral pH. Examples of commercially available carbomers that may be present in the matrix of the dosage forms of the present invention include Carbopol® 934P NF, Carbopol® 974P NF and Carbopol® 971P NF, available from Lubrizol.

Polyuronic Acids

The matrix of the dosage forms of the present invention may comprise a polyuronic acid, preferably a water-soluble polyuronic acid. Examples of water-soluble salts of polyuronic acid that may be used in the matrix include alkali metal salts of alginic acid and alkali metal salts of pectic acid. In preferred matrices, the water-soluble salt of polyuronic acid is a salt of alginic acid, which is actually a mixture of two polyuronic acids, namely, mannuoronic acid and guluronic acid. Examples of alkali metal salts of alginic acid that may be used in the matrices of the dosage forms of the present invention include sodium alginate, potassium alginate and ammonium alginate. A mixture of the same or different alginic acid salts of the same or different viscosities may be used.

Silicones

The matrix of the dosage forms of the present invention may comprise a silicone, preferably a silicone that can be cured at a temperature of less than 100° C. Particularly preferred silicones are those comprising polydiorganosiloxanes having silicon-bonded unsaturated organic groups, e.g. vinyl groups, available for reaction with polydiorganosiloxanes having silicon-bonded hydrogen atoms. Suitable silicones are described in EP-A-0425154, the entire content of which is incorporated herein by reference.

The matrix of the dosage forms of the present invention may optionally comprise a lubricant. Preferred lubricants are those that are described above in relation to the composition of the particulates. The amount of lubricant present in the matrix is preferably in the range 1-10% wt, preferably 2-5% wt, based on the total weight of the matrix.

The matrix of the dosage forms of the present invention may additionally contain other excipients that are conventional in the art, e.g. diluents, binders, granulating aids, colourants, flavourants, glidants, wet-regulating agents and disintegrants. The skilled man will readily be able to determine appropriate quantities of each of these excipients.

Preferably, the dosage forms of the present invention comprise 15-80% wt, more preferably 20-60% wt, still more preferably 30-55% wt, yet more preferably 35-45% wt of particulates, based on the total weight of the dosage form. Preferably, the dosage forms of the present invention comprise 20-85% wt, more preferably 30-70% wt, still more preferably 45-65% wt, yet more preferably 50-60% wt of matrix, based on the total weight of the dosage form. An advantage of the dosage forms of the present invention is that the same particulates may be mixed with matrix material in different amounts to thereby produce dosage forms of different strengths. Moreover, because the dosage forms of the invention have excellent tamper resistance properties, high strength dosage forms providing drug release over extended periods of time may be prepared. Advantageously, such dosage forms may only need to be dosed once or twice per day.

The dosage forms of the present invention may be prepared by any conventional method. Preferably, however, the dosage forms are prepared by compression. Thus, particulates as hereinbefore defined are preferably mixed, e.g. blended and/or granulated (e.g. wet granulated), with matrix material and the resulting mix (e.g. blend or granulate) is then compressed, preferably in moulds, to form tablets. It is also envisaged that the particulates herein described may be incorporated into a matrix using other processes, such as by melt granulation (e.g. using fatty alcohols and/or water-soluble waxes and/or water-insoluble waxes) or high shear granulation, followed by compression.

When the matrix of the dosage form comprises a curable agent, e.g. PEO, the preparation process preferably also includes a step of heating the dosage form comprising the curable material, e.g. PEO, to a temperature of at least about 60° C., preferably at least about 65° C., more preferably at least about 70° C., e.g. 50-100° C. In particularly preferred methods, the dosage form is heated at a temperature of from about 60° C. to about 90° C., preferably from about 65° C. to about 85° C. or from about 70° C. to about 80° C. This heating or "curing" process gives the curable agent, e.g. PEO, its crush resistance properties. The heating or curing step is preferably carried out for a time period suitable to achieve the desired crush resistance properties. This may be, for example, at least 1 minute. In preferred methods for making the dosage forms of the present invention, curing is carried out for at least about 5 minutes, preferably at least about 15 minutes, more preferably at least about 30 minutes, still more preferably at least about 60 minutes, e.g. at least about 90 minutes. In particularly preferred methods curing is carried out for a time from about 1 minute to about 24 hours, preferably from about 5 minutes to about 12 hours, still more preferably from about 30 minutes to about 6 hours, e.g. from about 1 hour to about 3 hours. Curing is preferably carried out after formation of the dosage form.

The dosage forms of the present invention may optionally comprise a coating, e.g. a cosmetic coating. The coating is preferably applied after formation of the dosage form. The coating may be applied prior to or after the curing process. Preferred coatings are Opadry® coatings available from Colorcon. Other preferred coating are Opaglos® coatings, also commercially available from Colorcon.

The skilled man may readily determine an appropriate amount of drug to include in a dosage form. For instance, in the case of analgesics, the total amount of drug present in the dosage form is that sufficient to provide analgesia. The total amount of drug administered to a patient in a dose will vary depending on numerous factors including the nature of the drug, the weight of the patient, the severity of the pain, the nature of other therapeutic agents being administered etc. As mentioned above, an advantage of the dosage forms of the present invention is that different strength dosage forms can be easily prepared. As a general guide, the total amount of drug present in the dosage forms of the present invention may be in the range 1 to 500 mg, more preferably 2 to 200 mg, still more preferably 5 to 100 mg, e.g. about 10 to 50 mg. For instance when the drug is hydromorphone HCl the total amount of drug in the dosage form might be 2, 4, 6, 8, 10, 12, 14, 16, 18, 20, 24, 28 or 32 mg. When the drug is oxycodone HCl the total amount of drug in the dosage form might be 5, 10, 20, 30, 40, 50, 60, 70 or 80 mg.

Preferred dosage forms of the present invention release drug in a controlled release profile, e.g. when ingested and exposed to gastric fluids and then intestinal fluids. The precise release profile can be altered by, for example, varying the composition of the particulates, the composition of the matrix and/or the proportions of particulate and matrix.

Preferred dosage forms of the invention are extended-release dosage forms. As used herein the term "extended-release dosage form" has the same meaning as "sustained-release dosage form" and "prolonged-release dosage form" and refers to a dosage form that continues to release drug over a period of at least 6 hours, e.g. at least 12 hours, when measured in a USP apparatus 1 (basket) at 100 rpm in 900 ml simulated gastric fluid without enzymes (SGF) with 0% ethanol at 37° C. Thus, by way of example, at least 5%, e.g. at least 10%, of the drug (based on the total weight of drug originally present in the dosage form) may be released during the first hour (i.e. between 0 and 1 hour) of dissolution. Preferred dosage forms of the present invention continue to release drug over a period in the range of at least 8 to 12 hours when measured in a USP Apparatus 1 (basket) at 100 rpm in 900 ml simulated gastric fluid without enzymes (SGF) with 0% ethanol at 37° C. Other particularly preferred dosage forms of the present invention continue to release drug over a period in the range of at least 12 to 24 hours when measured in a USP Apparatus 1 (basket) at 100 rpm in 900 ml simulated gastric fluid without enzymes (SGF) with 0% ethanol at 37° C.

In further preferred dosage forms of the invention, the amount of drug released from the extended-release dosage form at 1 hour when measured in a USP Apparatus 1 (basket) at 100 rpm in 900 ml simulated gastric fluid without enzymes (SGF) with 0% ethanol at 37° C. is less than 20%, preferably less than 10%, more preferably less than 8%, e.g. less than 5% (based on the total weight of drug originally present in the dosage form). In other words, the dosage forms of the invention preferably do not have a high initial release rate. Rather, the dosage forms of the invention provide a controlled release throughout the release profile.

Further preferred dosage forms of the invention provide an in vitro release, when measured in a USP Apparatus 1 (basket) at 100 rpm in 900 ml simulated gastric fluid without enzymes (SGF) with 0% ethanol at 37° C., of about 0-30% wt based on the total weight of the dosage form (e.g. 10-20% wt based on the total weight of the dosage form) released after 1 hour and over 80% wt based on the total weight of the dosage form (e.g. 85-99% wt based on the total weight of the dosage form) released after 12 hours.

Other preferred dosage forms of the invention provide an in vitro release, when measured in a USP Apparatus 1 (basket) at 100 rpm in 900 ml simulated gastric fluid without enzymes (SGF) with 0% ethanol at 37° C., of about 0 to 30% wt based on the total weight of the dosage form (e.g. 10-20% wt based on the total weight of the dosage form) released after 1 hour and over 80% wt based on the total weight of the dosage form (e.g. 85-99% wt based on the total weight of the dosage form) released after 24 hours. In the case of these dosage forms, preferably 40-70% wt based on the total weight of the dosage form (e.g. 50-60% wt based on the total weight of the dosage form) is released after 12 hours.

When the drug present in the dosage form is hydromorphone or a salt thereof (e.g. hydromorphone HCl), the in vitro dissolution rate of the dosage form, when measured by the USP Paddle Method (as described in Pharmacopoeia XXI (1985) at 100 rpm in 900 ml aqueous buffer (pH between 1.6 and 7.2) at 37° C., is between 12.5 and 42.5% (by weight) hydromorphone released after 1 hour, between 25 and 55% (by weight) hydromorphone released after 2 hours, between 45 and 75% (by weight) hydromorphone released after 4 hours and between 55 and 85% (by weight) hydromorphone released after 6 hours, the in vitro release rate being independent of pH between pH 1.6 and 7.2 and such that the peak plasma level of hydromorphone obtained in vivo occurs between 2 and 4 hours after administration of the dosage form.

Preferably the dissolution rate is between 17.5 and 37.5% (by weight) hydromorphone released after 1 hour, between 30 and 50% (by weight) after 2 hours, between 50 and 70% (by weight) after 4 hours and between 60 and 80% (by weight) after 6 hours. Most preferably, the dissolution rate is between 22.5 and 32.5% (by weight) hydromorphone released after 1 hour, between 35 and 45% (by weight) after 2 hours, between 55 and 65% (by weight) after 4 hours and between 65 and 75% (by weight) after 6 hours.

As used in the paragraph above, "independent of pH" means that the difference, at any given time, between the amount of hydromorphone released at pH 1.6 and the amount released at any other pH up to, and including, pH 7.2 (when measured in vitro using the USP Paddle Method (as described in Pharmacopoeia XXI (1985)) at 100 rpm in 900 ml aqueous buffer) is 10% (by weight) or less the amounts released being, in all cases, a mean of at least three experiments.

As used in the paragraph above, "peak plasma level of hydromorphone obtained in vivo" refers to the maximum mean concentration of hydromorphone found in the plasma of at least six healthy volunteers, when the volunteers are subjected to a single dose, pharmacokinetic study.

Preferably, the peak plasma level of hydromorphone is obtained in vivo between 2.25 and 3.75 hours after administration of the dosage form.

When the drug present in the dosage form is oxycodone or a salt thereof (e.g. oxycodone HCl), the in vitro dissolution rate of the dosage form, when measured by the USP Paddle Method (as described in Pharmacopoeia XXII (1990)) at 100 rpm in 900 ml aqueous buffer (pH between 1.6 and 7.2) at 37° C. is between 12.5 and 42.5% (by weight) oxycodone released after 1 hour, between 25 and 56% (by weight) oxycodone released after 2 hours, between 45 and 75% (by weight) oxycodone released after 4 hours and between 55 and 85% (by weight) oxycodone released after 6 hours, the in vitro release rate being substantially independent of pH such that the peak plasma level of oxycodone obtained in vivo occurs between 2 and 4.5 hours after administration of the dosage form.

Preferably the dissolution rate is between 17.5 and 38% (by weight) oxycodone released after 1 hour, between 30 and 50% (by weight) after 2 hours, between 50 and 70% (by weight) after 4 hours and between 60 and 80% (by weight) after 6 hours. Most preferably, the dissolution rate is between 17.5 and 32.5% (by weight) oxycodone released after 1 hour, between 35 and 45% (by weight) after 2 hours, between 55 and 65% (by weight) after 4 hours and between 65 and 75% (by weight) after 6 hours.

As used in the paragraph above relating to oxycodone, the term "substantially independent of pH" means that the difference, at any given time, between the amount of oxycodone released at, e.g., pH 1.6, and the amount released at any other pH, e.g., pH 7.2 (when measured in vitro using the USP Paddle Method (as described in Pharmacopoeia XXII (1990)) at 100 rpm in 900 ml aqueous buffer) is 10% (by weight) or less, the amounts released being, in all cases, a mean of at least three experiments.

As used in the paragraph above relating to oxycodone, "peak plasma level of oxycodone obtained in vivo" refers to the maximum mean concentration of oxycodone found in the plasma of at least six healthy volunteers, when the volunteers are subjected to a single dose, pharmacokinetic study.

When the dosage form comprises oxycodone or a salt thereof (e.g. oxycodone HCl) and naloxone (e.g. naloxone HCl), the dosage form preferably releases 1 to 40% (by weight), preferably 5 to 35% (by weight), more preferably 10 to 30% (by weight) and even more preferably between 15 and 25% (by weight) of oxycodone and/or naloxone after 15 minutes, as determined by applying the USP Basket Method at pH 1.2 using HPLC. Preferred dosage forms release 15 to 20% (by weight), 20 to 25% (by weight), about 15% (by weight), about 20% (by weight) or about 25% (by weight) oxycodone and/or naloxone after 15 minutes as determined by the aforementioned method.

In another embodiment, dosage forms comprising oxycodone or a salt thereof (e.g. oxycodone HCl) and naloxone (e.g. naloxone HCl) release 25 to 65% (by weight), preferably 30 to 60% (by weight), more preferably 35 to 55% (by weight) and even more preferably between 40 and 50% (by weight) of oxycodone and/or naloxone after 1 hour, as determined by applying the USP Basket Method at pH 1.2 using HPLC. Preferred dosage forms release 40 to 45% (by weight), 45 to 50% (by weight), about 40% (by weight), about 45% (by weight) or about 50% (by weight) oxycodone and/or naloxone after 1 hour as determined by the aforementioned method.

In another embodiment, dosage forms comprising oxycodone or a salt thereof (e.g. oxycodone HCl) and naloxone (e.g. naloxone HCl) release 40 to 80% (by weight), preferably 45 to 75% (by weight), more preferably 45 to 70% (by weight) and even more preferably between 45 to 50% (by weight), 50 to 55% (by weight), 55 to 60% (by weight), 60 to 65% (by weight) or 65 to 70% (by weight) of oxycodone and/or naloxone after 2 hours, as determined by applying the USP Basket Method at pH 1.2 using HPLC. Preferred dosage forms release about 45% (by weight), about 50% (by weight), about 55% (by weight), about 60% (by weight), about 65% (by weight) or about 70% (by weight) oxycodone and/or naloxone after 2 hours as determined by the aforementioned method.

In another embodiment, dosage forms comprising oxycodone or a salt thereof (e.g. oxycodone HCl) and naloxone (e.g. naloxone HCl) release 70 to 100% (by weight), preferably 75 to 95% (by weight), more preferably 80 to 95% (by weight) and even more preferably between 80 and 90% (by weight) of oxycodone and/or naloxone after 4 hours, as determined by applying the USP Basket Method at pH 1.2 using HPLC. Preferred dosage forms release 80 to 85% (by weight), 85 to 90% (by weight), about 80% (by weight), about 85% (by weight) or about 90% (by weight) oxycodone and/or naloxone after 4 hours as determined by the aforementioned method.

In another embodiment, dosage forms comprising oxycodone or a salt thereof (e.g. oxycodone HCl) and naloxone (e.g. naloxone HCl) release 70 to 100% (by weight), preferably 75 to 100% (by weight), more preferably 80 to 95% (by weight) and even more preferably between 80 and 85% (by weight), between 85 to 90% (by weight) or between 90 to 95% (by weight) of oxycodone and/or naloxone after 7 hours, as determined by applying the USP Basket Method at pH 1.2 using HPLC. Preferred dosage forms release about 80% (by weight), about 85% (by weight), about 90% or about 95% (by weight) oxycodone and/or naloxone after 7 hours as determined by the aforementioned method.

In another embodiment, dosage forms comprising oxycodone or a salt thereof (e.g. oxycodone HCl) and naloxone (e.g. naloxone HCl) release 85 to 100% (by weight), preferably 90 to 100% (by weight), more preferably 95 to 100% (by weight) and even more preferably between 97 and 100% (by weight) of oxycodone and/or naloxone after 12 hours, as determined by applying the USP Basket Method at pH 1.2 using HPLC.

A further advantage of the dosage forms of the present invention that arises from the fact that the drug is protected within the matrix of the dosage form is that the drug undergoes little, if any, degradation. In preferred dosage forms, the loss of the drug by degradation is less than 10% (by weight), preferably less than 5% (by weight), still more preferably less than 1% (by weight), after exposure to accelerated storage conditions of 40° C. and 75% relative humidity over 6 months.

The particulates and dosage forms of the present invention may be used in medicine, e.g. as an analgesic. The particulates and dosage forms are therefore particularly suitable for the treatment or management of pain. In such dosage forms, the drug is preferably an analgesic.

BRIEF DESCRIPTION OF THE DRAWINGS

The invention will now be described by the following non-limiting examples, wherein.

DETAILED DESCRIPTION OF PREFERRED EMBODIMENTS

Testing Procedures

In Vitro Dissolution Rate

The tablets are tested in vitro using standard procedures, e.g. USP Apparatus 1 (basket) or USP Apparatus 2 (paddle) at e.g. 50 rpm in e.g. 900 ml simulated gastric fluid without enzymes (SGF) at 37° C., using a Perkin Elmer UVVIS Spectrometer Lambda 20, UV at an appropriate wavelength for detection of the drug present therein. Particulates, uncured tablets, cured tablets and tampered, i.e. flattened particulates or tablets may be tested. Tampered tablets/particulates are flattened with a hammer using 7 manually conducted hammer strikes to impart physical tampering. The tablet/particulate dimensions before and after the flattening and the dissolution profiles are evaluated on separate samples.

Figure 1:
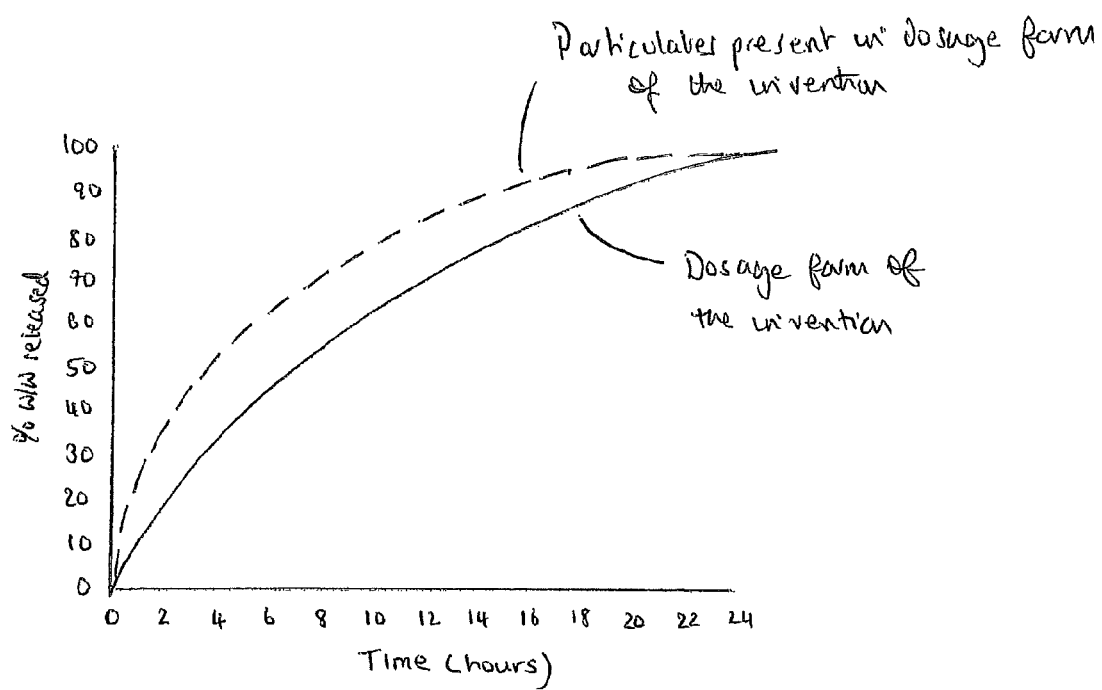
FIG. 1 shows a hypothetical dissolution rate for the particulates present in the dosage forms of the invention as well as for a dosage form per se.

The dissolution rate for the particulates present in the dosage form of the invention as well as for a dosage form per se is shown in FIG. 1. FIG. 1 shows that the release rate of drug from the particulates is higher than that from the dosage form. However the release rate of drug from the particulates is not sufficiently high for an abuser to achieve a euphorigenic effect. Thus even if an abuser crushes a dosage form of the present invention, the release rate of drug would not be significantly increased. This reduces the motivation of an abuser to try to tamper with a dosage form.

Tamper Resistance Test (i) Crushability

Cured tablets are subjected to a breaking strength test applying a force of a maximum of 196 Newtons using a Schleuniger 2E/106 Apparatus to evaluate the resistance to breaking. The particulates may be subjected to the same or a similar breaking strength test.

(ii) Resistance to Ethanol Extraction

Tablets are tested in vitro using ethanol/SGF media at ethanol concentrations of 0%, 20% and 40% to evaluate alcohol extractability. Testing is performed using standard procedures, e.g. USP Apparatus 1 (basket) or USP Apparatus 2 (paddle) at e.g. 50 rpm in e.g. 500 ml of media at 37° C., using a Perkin Elmer UV/VIS Spectrometer Lambda 20, UV at an appropriate wavelength for detection of the drug present therein. Sample time points include 0.5 and 1 hour.

Example 1

Particulates having the compositions summarised in Table 1 below are prepared as follows:

|  | Particulates A % w/w | Particulates B % w/w |
| --- | --- | --- |
| Hydromorphone HCl | 10 | 10 |
| Naloxone HCl | 20 | 20 |
| Ethylcellulose | 29 | 27 |
| Triethyl citrate | 2.9* | 5.4** |
| Stearyl alcohol | 10 | 10 |
| Glyceryl dibehenate | 3.0 | 3.0 |
| Eudragit NE 40D | 25.1 | 24.6 |

*10% based on ethyl cellulose
**20% based on ethyl cellulose

An ethylcellulose/triethyl citrate preparation is initially prepared by placing ethylcellulose in a blender and gradually adding, e.g. by spraying, triethyl citrate. Mixing is continued until a uniform blend is obtained then the mixture is allowed to stand overnight so that the triethyl citrate can penetrate through the ethylcellulose.

Hydromorphone HCl, naloxone HCl, stearyl alcohol, glyceryl dibehenate and the above-prepared ethylcellulose/triethyl citrate preparation are then added to a blender and mixed. The resulting mixture is granulated with an aqueous dispersion of Eudragit® NE 40D. The granulate is then dried to constant weight.

The dried granulate is then extruded. The melt extruder is set to predetermined extrusion conditions and extrusion is carried out. The extrudate obtained has an average diameter of 1 mm. The extrudate is then stretched by the conveyor belt and nip rollers during its transfer to the pelletiser. The stretched extrudate has an average diameter of about 500 μm. The stretched extrudate is then cut into particulates having an average length of about 500 μm.

Tablets having the compositions summarised in Table 2 below are prepared as follows:

TABLE 2

|  | Tablet 1 | Tablet 2 | Tablet 3 | Tablet 4 |
|---|---|---|---|---|
| Particulates (mg) | 40 | 80 | 160 | 240 |
| Matrix material (mg) | 58 | 116 | 232 | 348 |
| Lubricant (mg) | 2 | 4 | 8 | 12 |
| Total weight (mg) | 100 | 200 | 400 | 600 |

The particulates are blended with the matrix material and optionally other excipients. The lubricant is then added and the mixture is blended to form a uniform blend. The blend is then compressed in a suitable tool to the predetermined weight and thickness of tablet.

Coating and curing may subsequently be carried out in a single piece of equipment. If coating is required before curing, the tablet is heated to a predetermined temperature, spray coated and dried, before increasing the temperature to that required for curing. If curing is required prior to coating, the tablet is heated to the required temperature for a predetermined time then cooled. Spray coating may then optionally be carried out to a predetermined weight gain.

Example 2

Melt-extruded particulates with the composition as summarised in Table 3 below were produced by firstly preparing (by fluid bed granulation) placebo granules with the composition as summarised in Table 4 below, secondly milling the placebo granules (using a Retsch mill with a 0.5 mm screen), thirdly blending the milled placebo granules with hydromorphone hydrochloride, naloxone hydrochloride and magnesium stearate in a suitably sized cone blender to produce blended granules, and lastly melt extruding the blended granules in a Leistritz Micro 27 melt extruder to obtain an extrudate that is stretched and finally cut with a pelletiser to obtain the melt-extruded particulates.

The particulates obtained had an average diameter of 0.80 mm and an average length of 0.84 mm.

TABLE 3

|  | Example 2 (melt-extruded particulates) mg/unit |
|---|---|
| Hydromorphone HCl | 4 |
| Naloxone HCl | 8 |

TABLE 3-continued

|  | Example 2 (melt-extruded particulates) mg/unit |
|---|---|
| Eudragit NE 40 D | 40 (S) |
| Ethylcellulose (N10) | 25.8 |
| Hydroxypropyl methylcellulose (Methocel E5) | 0.15 |
| Glycerly monostearate | 2 |
| Talc | 20 |
| Lactose (anhydrous) | 4 |
| Stearyl alcohol | 5 |
| Glycerol dibehenate | 3 |
| Magnesium stearate | 1 |
| Total | 113 |

(S) = Solid content

TABLE 4

|  | Example 2 (placebo granules) mg/unit |
|---|---|
| Eudragit NE 40 D | 40 (S) |
| Ethylcellulose (N10) | 25.8 |
| Hydroxypropyl methylcellulose (Methocel E5) | 0.15 |
| Glycerly monostearate | 2 |
| Talc | 20 |
| Lactose (anhydrous) | 4 |
| Stearyl alcohol | 5 |
| Glycerol dibehenate | 3 |
| Total | 100 |

(S) = Solid content

Tablets with the composition as summarised in Table 5 below were manufactured by blending the particulates with hydroxypropyl methylcellulose (Methocel K4M) and magnesium stearate, followed by direct compression (using a Manesty F3 Betapress) of the resulting blend.

TABLE 5

|  | Example 2 (Tablets) (mg/unit) |
|---|---|
| Hydromophone/Naloxone particulates (4 mg/8 mg per unit) | 113 |
| Hydroxypropyl methylcellulose (Methocel K4M) | 56.5 |
| Magnesium stearate | 1.7 |
| Total | 171 |

Example 3

A lab scale batch of tablets with the composition as summarised in Table 6 below was manufactured by wet granulating the particulates of Example 2 (see Table 3) with the various excipients (water was used as a liquid binder and hydroxypropyl methylcellulose (Methocel K4M) as a binder) in a Kenwood processor, followed by compression of the resulting granulate using a Manesty F3 Betapress.

TABLE 6

|  | Example 3 (mg/unit) |
| --- | --- |
| Hydromophone/Naloxone particulates (4 mg/8 mg) | 113 |
| Hydroxypropyl methylcellulose (Methocel K4M) | 113 |
| Lactose | 57 |
| Magnesium stearate | 2.26 |
| Purified water | q.s. |
| Total | 285 |

Figure 2:
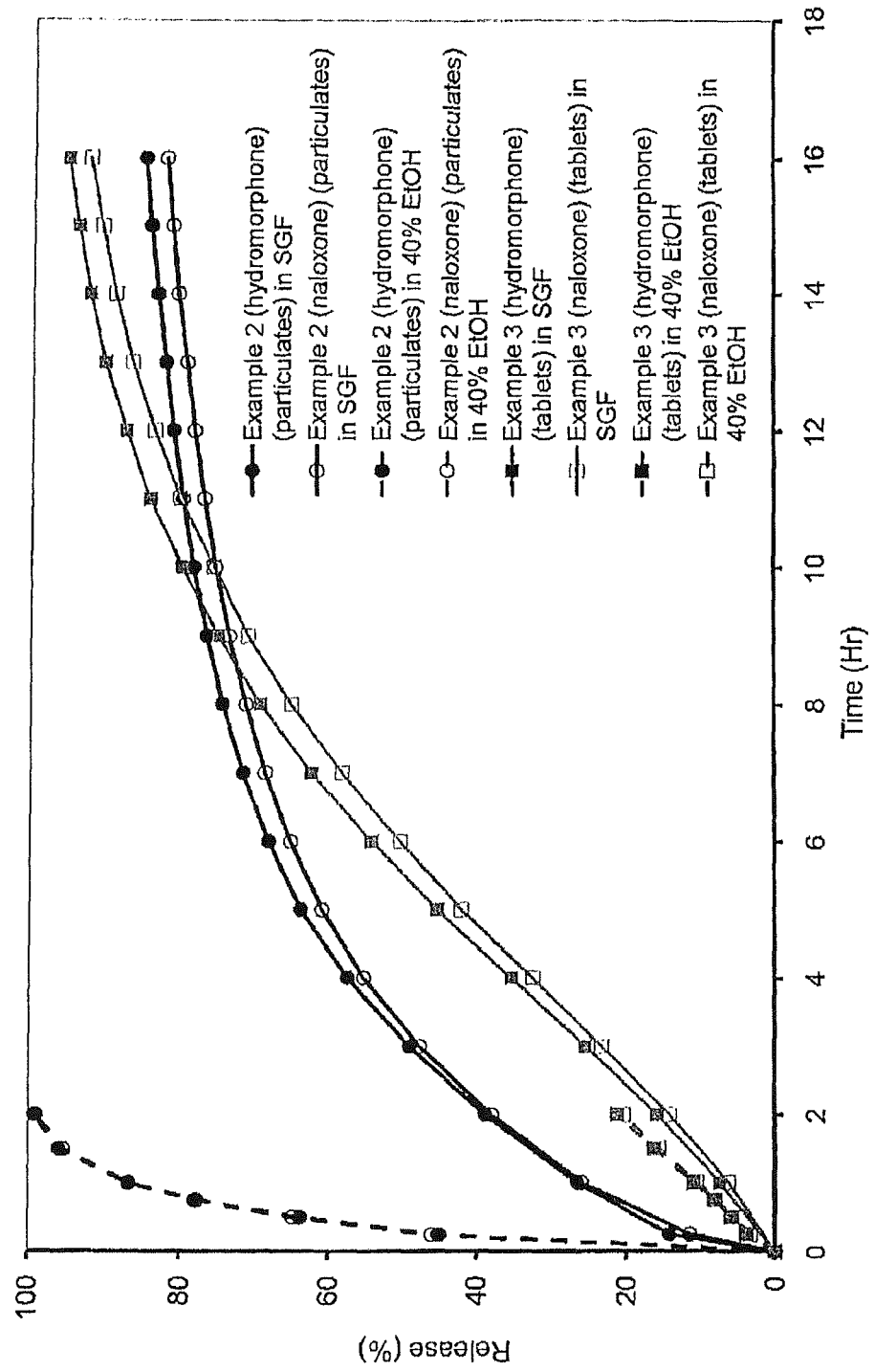
FIGS. 2-7 show the in vitro dissolution rate for the particulates present in the dosage forms of the invention as well as for a dosage form per se.

The particulates and tablets were tested for dissolution using Ph.Eur paddle dissolution apparatus at 37° C., 75 rpm separately in 500 ml of simulated gastric fluid without enzyme (SGF) at pH 1.2 and in 500 ml of 40% ethanol. Standard HPLC procedures were used for assay to measure the in vitro release rates, and the results obtained are plotted in accompanying FIG. 2.

Example 4

Tablets with the composition as summarised in Table 7 below were manufactured by the following process:
1. The particulates of Example 2 and lactose were loaded into the bowl of a Kenwood mixer and dry mixed.
2. Water was added dropwise to granulate the mixture until large granules were obtained.
3. HPMC (Methocel K100M) was added to the wet granules with continuous mixing.
4. Additional water was added as the mix was powdery.
5. The granules were dried in Gallenkamp oven for 2 hours at 50-55° C.
6. The dried granules were blended with magnesium stearate in a Pharmatech blender.
7. The blend was compressed into tablets using a Manesty F3 Betapress.

TABLE 7

|  | Example 4 (mg/unit) |
| --- | --- |
| Hydromophone/Naloxone particulates (4 mg/8 mg) | 113 |
| Hydroxypropyl methylcellulose (Methocel K100M) | 113 |
| Lactose | 57 |
| Magnesium stearate | 2.26 |
| Purified water | q.s. |
| Total | 285 |

Figure 3:
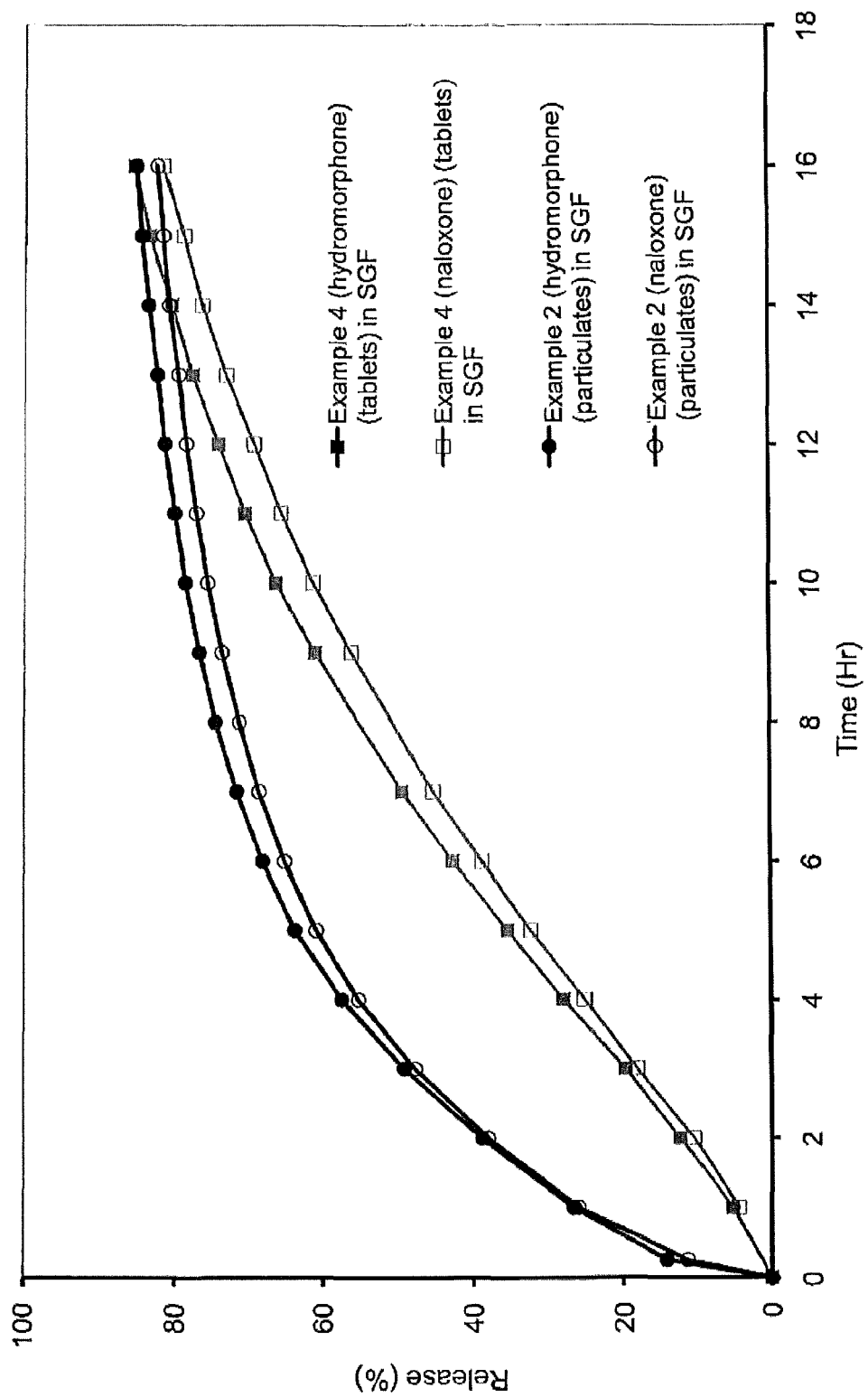

The particulates and tablets were tested for dissolution using Ph.Eur paddle dissolution apparatus at 37° C., 75 rpm in 500 ml of SGF at pH 1.2. Standard HPLC procedures were used for assay to measure the in vitro release rates, and the results obtained are plotted in accompanying FIG. 3.

Example 5

Tablets with the composition as summarised in Table 8 below were manufactured by the following process:
1. The particulates of Example 2 and lactose were loaded into a bowl and dry mixed.
2. Water was added dropwise to over-wet the mixture until large granules were obtained.
3. PEO was added to the wet granules with continuous mixing.
4. The granules were dried in a Gallenkamp oven for 2 hours at 50-55° C.
5. The dried granules were blended with magnesium stearate in a Pharmatech blender.
6. The blend was compressed into tablets using a Manesty F3 Betapress.
7. The resulting tablets were cured at 72° C. for 1 hour in an oven.

TABLE 8

|  | Example 5 (mg/unit) |
| --- | --- |
| Hydromophone/Naloxone particulates (4 mg/8 mg) | 113 |
| Polyethylene oxide (Polyox WSR-301) | 113 |
| Lactose | 57 |
| Magnesium stearate | 2.26 |
| Purified water | q.s. |
| Total | 285 |

Figure 4:
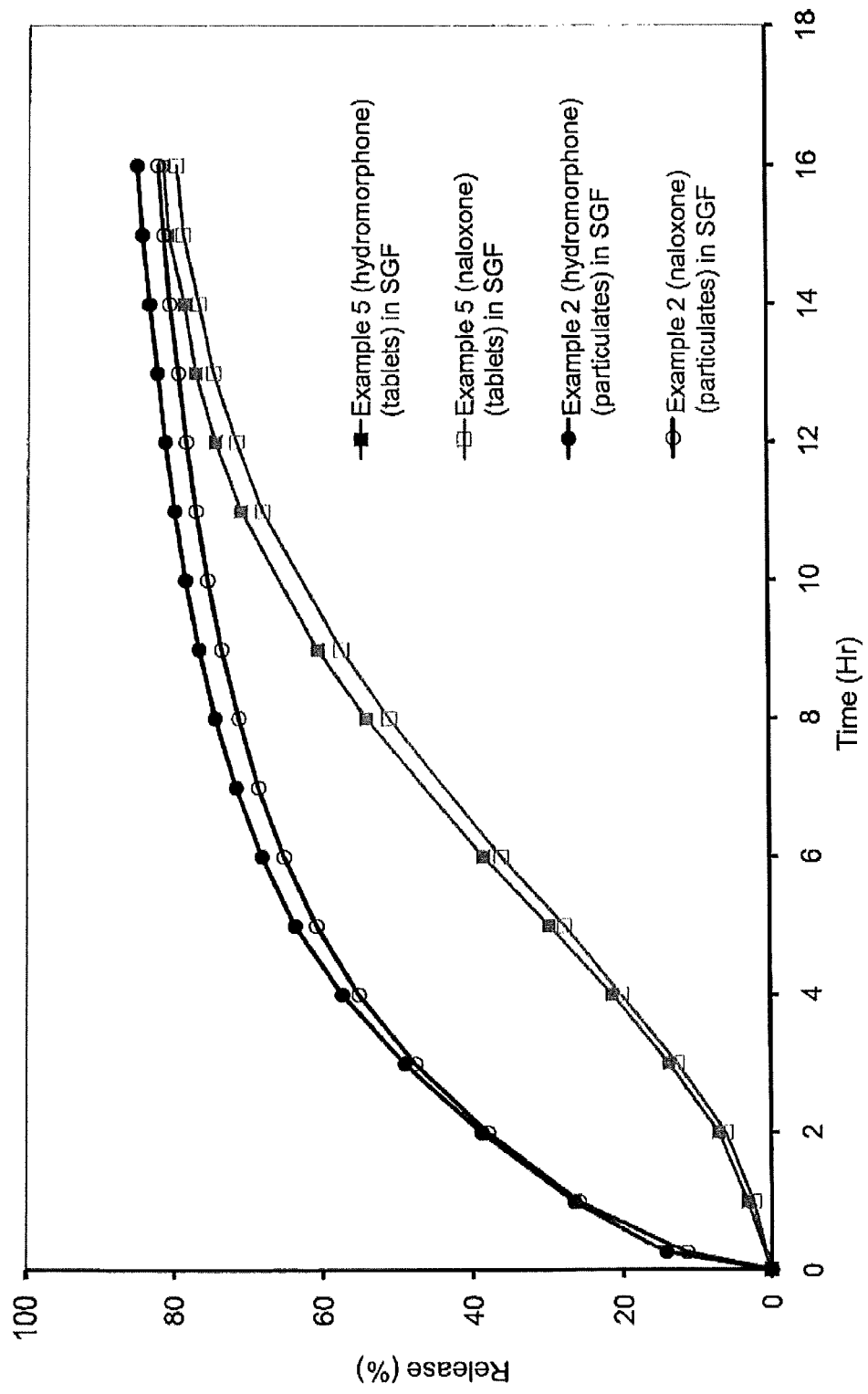
Figure 5:
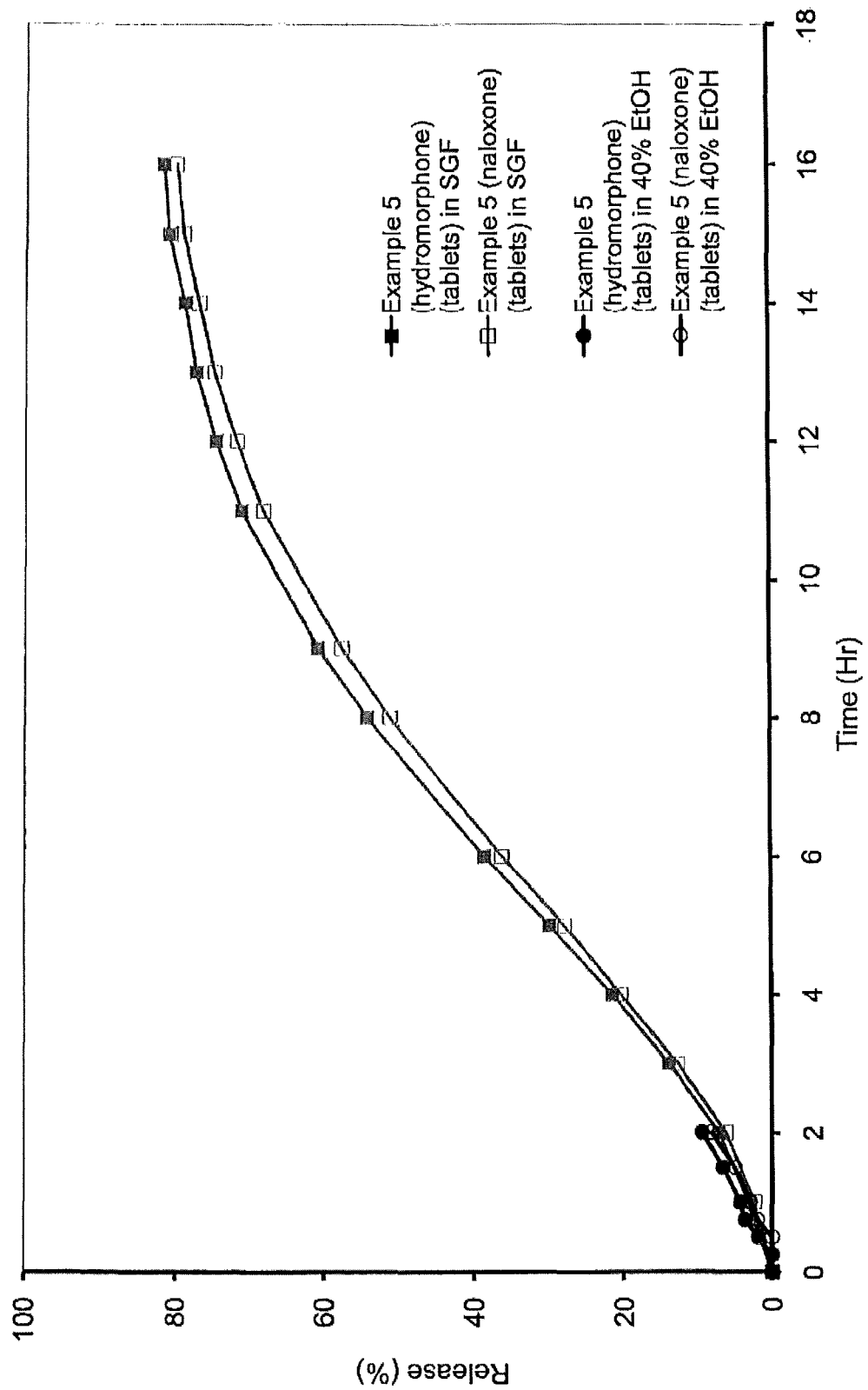

The particulates and tablets were tested for dissolution in SGF as for Example 4. The tablets were additionally tested for dissolution in 40% ethanol as for Example 3. Standard HPLC procedures were used for assay to measure the in vitro release rates, and the results obtained are plotted in accompanying FIGS. 4 and 5.

Example 6

Melt-extruded particulates with the composition as summarised in Table 9 below were produced by firstly preparing (by fluid bed granulation) placebo granules with the composition as summarised in Table 10 below, secondly milling the placebo granules (using a Retsch mill with a 0.5 mm screen), thirdly blending the milled placebo granules with hydromorphone hydrochloride, naloxone hydrochloride and magnesium stearate and sodium lauryl sulphate (2 mg/unit) in a suitably sized cone blender to produce blended granules, and lastly melt extruding the blended granules in a Leistritz Micro 27 melt extruder to obtain an extrudate that is stretched and finally cut with a pelletiser to obtain the melt-extruded particulates.

The particulates obtained had an average diameter of 0.82 mm and an average length of 0.81 mm.

TABLE 9

|  | Example 6 (melt-extruded particulates) mg/unit |
| --- | --- |
| Hydromorphone HCl | 4 |
| Naloxone HCl | 8 |
| Eudragit NE 40 D | 30 (S) |
| Ethylcellulose (N10) | 47.3 |
| Hydroxypropyl methylcellulose (Methocel E5) | 0.23 |
| Glycerly monostearate | 4.5 |
| Talc | 5 |
| Lactose (anhydrous) | 4 |
| Stearyl alcohol | 5 |

TABLE 9-continued

|  | Example 6 (melt-extruded particulates) mg/unit |
| --- | --- |
| Glycerol dibehenate | 2 |
| Sodium lauryl sulphate | 4 |
| Magnesium stearate | 1 |
| Total | 115 |

(S) = Solid content

TABLE 10

|  | Example 6 (placebo granules) mg/unit |
| --- | --- |
| Eudragit NE 40 D | 30 (S) |
| Ethylcellulose (N10) | 47.3 |
| Hydroxypropyl methylcellulose (Methocel E5) | 0.23 |
| Glycerly monostearate | 4.5 |
| Talc | 5 |
| Lactose (anhydrous) | 4 |
| Stearyl alcohol | 5 |
| Glycerol dibehenate | 2 |
| Sodium lauryl sulphate | 2 |
| Total | 100 |

(S) = Solid content

Tablets with the composition as summarised in Table 11 below were manufactured by the process of Example 5 but without step 7 (tablet curing), and except that in step 1 the particulates of this example, instead of Example 2, were dry mixed with lactose and trisodium citrate, and in step 3 sodium alginate, instead of PEO, was added to the wet granules with continuous mixing.

TABLE 11

|  | Example 6 (mg/unit) |
| --- | --- |
| Hydromophone/Naloxone particulates (4 mg/8 mg) | 115 |
| Sodium alginate | 113 |
| Lactose | 28.5 |
| Trisodium citrate | 28.5 |
| Magnesium stearate | 2.26 |
| Purified water | q.s. |
| Total | 287 |

Example 7

Tablets with the composition as summarised in Table 12 below were manufactured by the process of Example 5 but without step 7 (tablet curing), and except that in step 1 the particulates of Example 6, instead of Example 2, were dry mixed with lactose and magnesium stearate, and in step 3 xanthan gum, instead of PEO, was added to the wet granules with continuous mixing.

TABLE 12

|  | Example 7 (mg/unit) |
| --- | --- |
| Hydromophone/Naloxone particulates (4 mg/8 mg) | 115 |
| Xanthan gum | 113 |
| Lactose | 57 |
| Magnesium stearate | 2.26 |
| Purified water | q.s. |
| Total | 287 |

Figure 6:
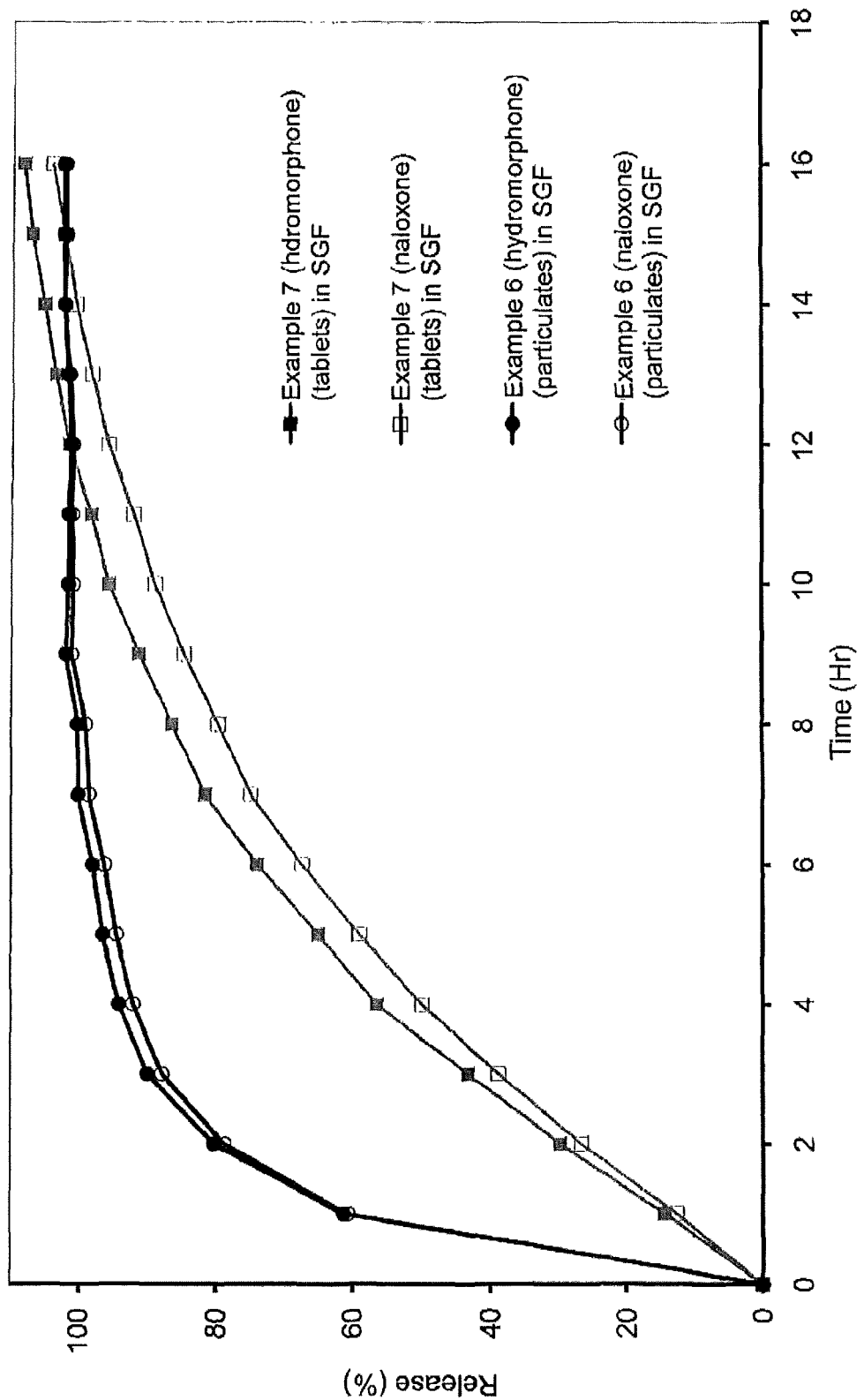
Figure 7:
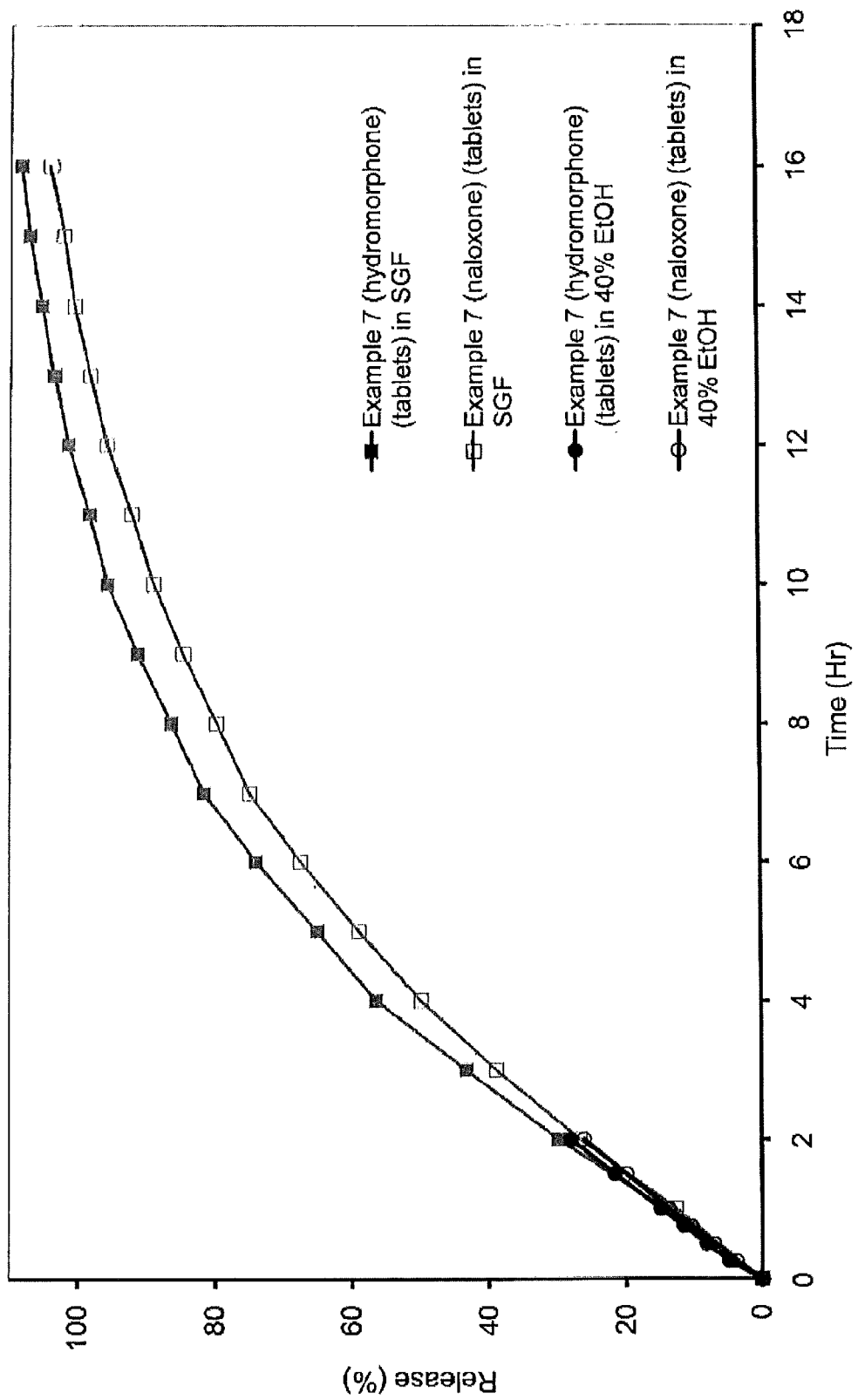

The particulates and tablets were tested for dissolution in SGF as for Examples 4 and 5. The tablets were additionally tested for dissolution in 40% ethanol as for Examples 3 and 5. Standard HPLC procedures were used for assay to measure the in vitro release rates, and the results obtained are plotted in accompanying FIGS. 6 and 7.

The invention claimed is:

1. A dosage form comprising: melt-extruded particulates comprising a drug which is an opioid agonist and a copolymer of acrylic acid alkyl esters and methacrylic acid alkyl esters or mixtures thereof; and a matrix; wherein said melt-extruded particulates have an average diameter of 200-800 μm and are present as a discontinuous phase in said matrix; wherein said matrix is a continuous phase comprising a gel-forming agent selected from polyethylene oxide which has an average molecular weight of at least 1,000,000, polyvinyl alcohol, hydroxypropyl methyl cellulose, carbomers, poly(uronic) acids, or mixtures thereof; wherein said dosage form comprises 30-55% wt of said melt-extruded particulates and 45-70% wt of said matrix, based on the total weight of the dosage form.

2. The dosage form as claimed in claim 1, wherein said melt-extruded particulates are stretched melt-extruded particulates.

3. The dosage form as claimed in claim 1, in the form of a tablet.

4. The dosage form as claimed in claim 1, wherein said dosage form is tamper resistant.

5. The dosage form as claimed in claim 1, wherein the amount of drug released from the dosage form at 0.5 hour when measured in a USP Apparatus 1 (basket) at 100 rpm in 900 ml simulated gastric fluid without enzymes (SGF) with 40% ethanol at 37° C., is within ±20% of the amount of drug released from the dosage form at 0.5 hour when measured in a USP Apparatus 1 (basket) at 100 rpm in 900 ml simulated gastric fluid without enzymes (SGF) with 0% ethanol at 37° C.

6. The dosage form as claimed in claim 1, wherein said melt-extruded particulates have a breaking strength of at least 350 Newtons.

7. The dosage form as claimed in claim 1, wherein said melt-extruded particulates are microparticulates.

8. The dosage form as claimed in claim 1, wherein said melt-extruded particulates have a length of less than 1000 μm.

9. The dosage form as claimed in claim 1, wherein said opioid agonist is selected from the group consisting of oxycodone, oxymorphone, hydrocodone, hydromorphone, morphine, codeine, buprenorphine, fentanyl, tramadol, tapentadol and pharmaceutically acceptable salts thereof.

10. The dosage form as claimed in claim 1, wherein said melt-extruded particulates comprise 3 to 50% wt of drug, based on the total weight of a melt-extruded particulate.

11. The dosage form as claimed in claim 1, further comprising one or more additional active ingredients.

12. The dosage form as claimed in claim 1, wherein said melt-extruded particulates comprise 10 to 50% wt of said copolymer based on the total weight of a melt-extruded particulate.

13. The dosage form as claimed in claim 1, wherein said melt-extruded particulates further comprise a rate controlling or modifying agent.

14. The dosage form as claimed in claim 13, wherein said melt-extruded particulates comprise 20 to 50% wt of rate controlling or modifying agent, based on the total weight of the melt-extruded particulate.

15. The dosage form as claimed in claim 13, wherein said rate controlling or modifying agent is an alkyl cellulose.

16. The dosage form as claimed in claim 15, wherein said alkyl cellulose is ethylcellulose.

17. The dosage form as claimed in claim 1, wherein said melt-extruded particulates further comprise a lubricant.

18. The dosage form as claimed in claim 1, wherein said melt-extruded particulates further comprise a plasticiser.

19. The dosage form as claimed in claim 1, wherein said melt-extruded particulates comprise oxycodone or hydromorphone, an ethyl acrylate and methyl methacrylate copolymer, ethyl cellulose as rate controlling or modifying agent, stearyl alcohol and/or triethyl citrate as plasticiser, glyceryl dibehenate as lubricant and optionally an opioid antagonist.

20. The dosage form as claimed in claim 19, wherein said oxycodone or hydromorphone is present as its hydrochloride salt.

21. The dosage form as claimed in claim 1, wherein said melt-extruded particulates comprise an opioid agonist and further comprise an opioid antagonist.

22. The dosage form as claimed in claim 1, wherein said gel-forming agent is curable.

23. The dosage form as claimed in claim 1, wherein said dosage form can be flattened without breaking to a thickness of less than 60% of the thickness of the dosage form before flattening.

24. A process for preparing a dosage form as claimed in claim 1, comprising: mixing melt-extruded particulates comprising a drug which is an opioid agonist with a matrix material so that said melt-extruded particulates form a discontinuous phase in said matrix and said matrix forms a continuous phase, and forming said mixture into a dosage form comprising 30-55% wt of said melt-extruded particulates and 45-70% wt of said matrix, based on the total weight of the dosage form.

25. The process as claimed in claim 24, wherein said particulates are melt extruded at a temperature of 100° C. or less.

26. The process as claimed in claim 24, further comprising curing said matrix.

27. A process for preparing a dosage form as claimed in claim 1, comprising: mixing melt-extruded particulates with a matrix material to obtain a mixture so that said melt-extruded particulates form a discontinuous phase in said matrix and said matrix forms a continuous phase, and forming said mixture into a dosage form comprising 30-55% wt of said melt extruded particulates and 45-70% wt of said matrix, based on the total weight of the dosage form, wherein said melt-extruded particulates are optionally prepared by stretching and cutting a melt extrudate comprising a drug.

28. A process for preparing a dosage form as claimed in claim 1, comprising: i) melt extruding a composition comprising said drug which is an opioid agonist to than a melt extrudate; ii) optionally stretching said melt extrudate to form an optionally stretched extrudate; iii) cutting said optionally stretched extrudate to form particulates; iv) mixing said particulates with a matrix material to obtain a mixture so that said particulates form a discontinuous phase in said matrix and said matrix forms a continuous phase; and forming said mixture into a dosage form comprising 30-55% wt of said melt-extruded particulates and 45-70% wt of said matrix, based on the total weight of the dosage form.

29. A method of treating or managing pain, comprising treating or managing the pain with the dosage form of claim 1.

30. A method of treating a subject in need of pain relief, comprising administering to said subject in need of pain relief the dosage fonts as claimed in claim 1.

31. The dosage form as claimed in claim 1, wherein said copolymer is selected from the group consisting of poly (ethyl acrylate-co-methyl methacrylate-co-trimethylammonioethyl methacrylate chloride) 1:2:0.2, poly(ethyl acrylate-co-methyl methacrylate-co-trimethylammonioethyl methacrylate chloride) 1:2:0.1, and poly(ethyl acrylate-co-methyl methacrylate) 2:1.

32. The dosage form as claimed in claim 1, comprising 35-45% wt of said melt-extruded particulates, based on the total weight of the dosage form.

33. The dosage form as claimed in claim 1, wherein said melt-extruded particulates are blended or granulated, or both blended and granulated, with the matrix material and the resulting mix is compressed to form a plurality of tablets.

34. The dosage form as claimed in claim 1, wherein said melt-extruded particulates are blended or granulated, or both blended and granulated, with the matrix material in the form of a curable matrix material and the resulting mix is compressed to form a plurality of tablets, and said curable matrix material is then cured at a temperature of at least about 60° C.

35. The dosage form as claimed in claim 1, comprising 45-65% wt of said matrix, based on the total weight of the dosage form.

36. The dosage form as claimed in claim 1, comprising 50-60% wt of said matrix, based on the total weight of the dosage form.

37. The dosage form as claimed in claim 1 in the form of a tablet, wherein
said melt-extruded particulates are blended or granulated, or both blended and granulated, with the matrix material and the resulting mix is compressed to form said tablet.

38. The dosage form as claimed in claim 1 in the form of a tablet, wherein
said melt-extruded particulates are blended or granulated, or both blended and granulated, with the matrix material in the form of a curable matrix material and the resulting mix is compressed to form said tablet and said curable matrix material is then cured at a temperature of at least about 60° C.

39. The dosage form of claim 37, wherein said melt-extruded particulates and the matrix material are granulated by wet granulation.

40. The dosage form of claim 38, wherein said melt-extruded particulates and the matrix material are granulated by wet granulation.

41. The dosage form as claimed in claim 1, wherein said melt-extruded particulates have an average length of 200-800 μm.

* * * * *